US011000625B2

(12) United States Patent
Anseth et al.

(10) Patent No.: US 11,000,625 B2
(45) Date of Patent: May 11, 2021

(54) AMPLIFIED PHOTODEGRADATION OF HYDROGELS AND METHODS OF PRODUCING THE SAME

(71) Applicant: The Regents of the University of Colorado, a body Corporate, Denver, CO (US)

(72) Inventors: Kristi Anseth, Boulder, CO (US); Ian Marozas, Boulder, CO (US); Tobin Brown, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 15/995,815

(22) Filed: Jun. 1, 2018

(65) Prior Publication Data
US 2018/0361016 A1  Dec. 20, 2018

Related U.S. Application Data

(60) Provisional application No. 62/520,255, filed on Jun. 15, 2017.

(51) Int. Cl.
*A61L 26/00* (2006.01)
*A61L 27/52* (2006.01)
*C08J 3/075* (2006.01)
*C08K 5/5313* (2006.01)
*C08L 71/02* (2006.01)

(52) U.S. Cl.
CPC ......... *A61L 26/008* (2013.01); *A61L 26/0019* (2013.01); *A61L 26/0057* (2013.01); *A61L 27/52* (2013.01); *C08J 3/075* (2013.01); *A61L 2300/62* (2013.01); *A61L 2300/64* (2013.01); *C08J 2371/02* (2013.01); *C08K 5/5313* (2013.01); *C08L 71/02* (2013.01)

(58) Field of Classification Search
CPC ............. A61L 2300/62; A61L 2300/64; A61L 26/0019; A61L 26/0057; A61L 26/008; A61L 27/52; C08L 71/02; C08J 2371/02; C08J 3/075; C08K 5/5313
See application file for complete search history.

(56) References Cited

FOREIGN PATENT DOCUMENTS

WO   WO/2009/039307   3/1909

OTHER PUBLICATIONS

Grim et al.; J Control Release; Dec. 10, 2015; 219: 95-106.*
Brown et al.; Adv Mater.; Mar. 2017; 29(11). Originally published online Jan. 23, 2017.*
Annabi, N. et al. (2014) "25th Anniversary Article: Rational Design and Applications of Hydrogels in Regenerative Medicine," *Advanced Materials* 26(1), 85-124.
Ashley, G. W. et al. (2013) "Hydrogel drug delivery system with predictable and tunable drug release and degradation rates," *Proceedings of the National Academy of Sciences* 110(6), 2318-2323.
Azagarsamy, M. A. et al. (2016) 128—Synthesis of dynamic stem cell niches using bioorthogonal photo-click chemistries, in *PMSE: Division of Polymeric Materials Science and Engineering*, American Chemical Society, 251st American Chemical Society (ACS) National Meeting & Exposition. Spring 2016, Mar. 13-17, 2016.
Azagarsamy, M. A. et al. (2014) "Coumarin-Based Photodegradable Hydrogel: Design, Synthesis, Gelation, and Degradation Kinetics," *ACS Macro Letters* 3(6), 515-519.
Burdick, J. A. et al. (2002) "Photoencapsulation of osteoblasts in injectable RGD-modified PEG hydrogels for bone tissue engineering," *Biomaterials* 23(22), 4315-4323.
Caliari, S. R. et al. (2016) "Stiffening hydrogels for investigating the hepatic stellate cell mechanotransduction during myofibroblast activation," *Scientific Reports* 6, 21387.
Chang, P. V. et al. (2010) "Copper-free click chemistry in living animals," *Proceedings of the National Academy of Sciences* 107(5), 1821-1826.
Choudhury, S. et al. (2015) "A highly reversible room-temperature lithium metal battery based on crosslinked hairy nanoparticles," *Nature Communications* 6, 10101.
Deforest, C. A. et al. (2011) "Cytocompatible Click-based Hydrogels with Dynamically-Tunable Properties Through Orthogonal Photoconjugation and Photocleavage Reactions," *Nature Chemistry* 3(12), 925-931.
Deforest, C. A. et al. (2012) "Photoreversible Patterning of Biomolecules within Click-Based Hydrogels," *Angewandte Chemie International Edition* 51(8), 1816-1819.
Deforest, C. A. et al. (2009) "Sequential Click Reactions for Synthesizing and Patterning 3D Cell Microenvironments," *Nature Materials* 8(8), 659-664.
Deforest, C. A. et al. (2015) "A photoreversible protein-patterning approach for guiding stem cell fate in three-dimensional gels," *Nature Materials* 14(5), 523-531.
Ekkebus, R. et al. (2013) "On Terminal Alkynes That Can React with Active-Site Cysteine Nucleophiles in Proteases," *Journal of the American Chemical Society* 135(8), 2867-2870.
Evans, R. A. et al. (2000) "Free-Radical Ring-Opening Polymerization of Cyclic Allylic Sulfides. 2. Effect of Substituents on Seven- and Eight-Membered Ring Low Shrink Monomers," *Macromolecules* 33(18), 6722-6731.
Fairbanks, B. D. et al. (2009) "Photoinitiated polymerization of PEG-diacrylate with lithium phenyl-2,4,6-trimethylbenzoylphosphinate: polymerization rate and cytocompatibility," *Biomaterials* 30(35), 6702-6707.
Fairbanks, B. D. et al. (2009) "Thiol—Yne Photopolymerizations: Novel Mechanism, Kinetics, and Step-Growth Formation of Highly Cross-Linked Networks," *Macromolecules* 42(1), 211-217.
Fairbanks, B. D. et al. (2010) "Reaction Rates and Mechanisms for Radical, Photoinitated Addition of Thiols to Alkynes, and Implications for Thiol—Yne Photopolymerizations and Click Reactions," *Macromolecules* 43(9), 4113-4119.

(Continued)

*Primary Examiner* — Jeffrey T. Palenik
(74) *Attorney, Agent, or Firm* — Medlen & Carroll, LLP

(57) ABSTRACT

This invention is in the field of synthesis and amplified photodegradation of hydrogel network and methods of producing and using the same.

17 Claims, 11 Drawing Sheets

(56) References Cited

OTHER PUBLICATIONS

Gandavarapu, N. R. et al. (2014) "Photo-Click Living Strategy for Controlled, Reversible Exchange of Biochemical Ligands," *Advanced Materials* 26(16), 2521-2526.
Griffin, D. R. et al. (2012) "Photodegradable Macromers and Hydrogels for Live Cell Encapsulation and Release," *Journal of the American Chemical Society* 134(31), 13103-13107.
Griffin, D. R. et al. (2012) "Photoselective Delivery of Model Therapeutics from Hydrogels," *ACS Macro Letters* 1(11), 1330-1334.
Han, L.-H. et al. (2014) "Photo-crosslinkable PEG-Based Microribbons for Forming 3D Macroporous Scaffolds with Decoupled Niche Properties," *Advanced Materials* 26(11), 1757-1762.
Highley, C. B. et al. (2015) "Direct 3D Printing of Shear-Thinning Hydrogels into Self-Healing Hydrogels," *Advanced Materials* 27(34), 5075-5079.
Hinton, T. J. et al. (2015) "Three-dimensional printing of complex biological structures by freeform reversible embedding of suspended hydrogels," *Science Advances* 1(9).
Hoffman, A. S. (2012) "Hydrogels for biomedical applications," *Advanced Drug Delivery Reviews* 64, Supplement, 18-23.
Hudalla, G. A. et al. (2008) "An Approach to Modulate Degradation and Mesenchymal Stem Cell Behavior in Poly(ethylene glycol) Networks," *Biomacromolecules* 9(3), 842-849.
Jewett, J. C. et al. (2010) "Rapid Cu-Free Click Chemistry with Readily Synthesized Biarylazacyclooctynones," *Journal of the American Chemical Society* 132(11), 3688-3690.
Jiang, Y. et al. (2014) "Click hydrogels, microgels and nanogels: Emerging platforms for drug delivery and tissue engineering," *Biomaterials* 35(18), 4969-4985.
Khetan, S. et al. (2010) "Patterning network structure to spatially control cellular remodeling and stem cell fate within 3-dimensional hydrogels," *Biomaterials* 31(32), 8228-8234.
Khetan, S. et al. (2013) "Degradation-mediated cellular traction directs stem cell fate in covalently crosslinked three-dimensional hydrogels," *Nature Materials* 12(5), 458-465.
Kloxin, A. M. et al. (2010) "In situ elasticity modulation with dynamic substrates to direct cell phenotype," *Biomaterials* 31(1), 1-8.
Kloxin, A. M. et al. (2009) "Photodegradable hydrogels for dynamic tuning of physical and chemical properties," *Science* 324(5923), 59-63.
Kloxin, A. M. et al. (2010) "Mechanical properties of cellularly responsive hydrogels and their experimental determination," *Advanced Materials* 22(31), 3484-3494.
Kloxin, C. J. et al. (2013) "Covalent adaptable networks: smart, reconfigurable and responsive network systems," *Chemical Society Reviews* 42(17), 7161-7173.
Kloxin, C. J. et al. (2009) "Stress Relaxation via Addition—Fragmentation Chain Transfer in a Thiol-ene Photopolymerization," *Macromolecules* 42(7), 2551-2556.
Lee, K. Y. et al. (2012) "Alginate: properties and biomedical applications," *Progress in Polymer Science* 37(1), 106-126.
Lutolf, M. P. et al. (2003) "Synthetic matrix metalloproteinase-sensitive hydrogels for the conduction of tissue regeneration: Engineering cell-invasion characteristics," *Proceedings of the National Academy of Sciences* 100(9), 5413-5418.
Majima, T. et al. (1991) "Phenyl-2,4,6-trimethylbenzoylphosphinates as water-soluble photoinitiators. Generation and reactivity of O=P(C6H5)(O-) radical anions," *Die Makromolekulare Chemie* 192(10), 2307-2315.
Masaro, L. et al. (1999) "Self-Diffusion Studies of Water and Poly(ethylene glycol) in Solutions and Gels of Selected Hydrophilic Polymers," *Macromolecules* 32(13), 4375-4382.
Mccall, J. D. et al. (2012) "Thiol—Ene Photopolymerizations Provide a Facile Method to Encapsulate Proteins and Maintain Their Bioactivity," *Biomacromolecules* 13(8), 2410-2417.
Mckinnon, D. D. et al. (2014) "Design and Characterization of a Synthetically Accessible, Photodegradable Hydrogel for User-Directed Formation of Neural Networks," *Biomacromolecules* 15(7), 2808-2816.
Mckinnon, D. D. et al. (2014) "Biophysically Defined and Cytocompatible Covalently Adaptable Networks as Viscoelastic 3D Cell Culture Systems," *Advanced Materials* 26(6), 865-872.
Mckinnon, D. D. et al. (2014) "Bis-Aliphatic Hydrazone-Linked Hydrogels Form Most Rapidly at Physiological pH: Identifying the Origin of Hydrogel Properties with Small Molecule Kinetic Studies," *Chemistry of Materials* 26(7), 2382-2387.
Metters, A. T. et al. (2001) "A Statistical Kinetic Model for the Bulk Degradation of PLA-b-PEG-b-PLA Hydrogel Networks: Incorporating Network Non-Idealities," *Journal of Physical Chemistry B* 105, 8069-8076.
Moad, G. et al. (2008) "Radical addition—fragmentation chemistry in polymer synthesis," *Polymer* 49(5), 1079-1131.
Mosiewicz, K. A. et al. (2013) "In situ cell manipulation through enzymatic hydrogel photopatterning," *Nature Materials* 12(11), 1072-1078.
Nguyen, P. K. et al. (2013) "Clickable Poly(ethylene glycol)-Microsphere-Based Cell Scaffolds," *Macromolecular Chemistry and Physics* 214(8), 948-956.
Nichol, J. W. et al. (2010) "Cell-laden microengineered gelatin methacrylate hydrogels," *Biomaterials* 31(21), 5536-5544.
Norris, S. C. P. et al. (2016) "Direct Gradient Photolithography of Photodegradable Hydrogels with Patterned Stiffness Control with Submicrometer Resolution," *ACS Biomaterials Science & Engineering* 2(8), 1309-1318.
Rodell, C. B. et al. (2013) "Rational Design of Network Properties in Guest-Host Assembled and Shear-Thinning Hyaluronic Acid Hydrogels," *Biomacromolecules* 14(11), 4125-4134.
Rosales, A. M. et al. (2016) "The design of reversible hydrogels to capture extracellular matrix dynamics," *Nature Reviews Materials* 1, 15012.
Scott, T. F. et al. (2006) "Actuation in Crosslinked Polymers via Photoinduced Stress Relaxation," *Advanced Materials* 18(16), 2128-2132.
Scott, T. F. et al. (2005) "Photoinduced Plasticity in Cross-Linked Polymers," *Science* 308(5728), 1615.
Shiu, H.-Y. et al. (2009) "Electron-Deficient Alkynes as Cleavable Reagents for the Modification of Cysteine-Containing Peptides in Aqueous Medium," *Chemistry—A European Journal* 15(15), 3839-3850.
Shiu, H.-Y. et al. (2010) "A Highly Selective FRET-Based Fluorescent Probe for Detection of Cysteine and Homocysteine," *Chemistry—A European Journal* 16(11), 3308-3313.
Steinhilber, D. et al. (2013) "A Microgel Construction Kit for Bioorthogonal Encapsulation and pH-Controlled Release of Living Cells," *Angewandte Chemie International Edition* 52(51), 13538-13543.
Stockmayer, W. H. (1943) "Theory of molecular size distribution and gel formation in branched-chain polymers," *Journal of Chemical Physics* 11-55, 45.
Stowers, R. S. et al. (2015) "Dynamic phototuning of 3D hydrogel stiffness," *Proceedings of the National Academy of Sciences of the United States of America* 112(7), 1953-1958.
Tamura, M. et al. (2015) "Click-crosslinkable and photodegradable gelatin hydrogels for cytocompatible optical cell manipulation in natural environment," *Scientific Reports* 5, 15060.
Tibbitt, M. W. et al. (2013) "Modeling controlled photodegradation in optically thick hydrogels," *Journal of Polymer Science Part A: Polymer Chemistry* 51(9), 1899-1911.
Tsang, K. M. C. et al. (2015) "Facile One-Step Micropatterning Using Photodegradable Gelatin Hydrogels for Improved Cardiomyocyte Organization and Alignment," *Advanced Functional Materials* 25(6), 977-986.
Van Geel, R. et al. (2012) "Preventing Thiol-Yne Addition Improves the Specificity of Strain-Promoted Azide—Alkyne Cycloaddition," *Bioconjugate Chemistry* 23(3), 392-398.
Wang, H. et al. (2015) "Adaptable Hydrogel Networks with Reversible Linkages for Tissue Engineering," *Advanced Materials* 27(25), 3717-3736.

(56) References Cited

OTHER PUBLICATIONS

Wong, D. Y. et al. (2015) "Low-Dose, Long-Wave UV Light Does Not Affect Gene Expression of Human Mesenchymal Stem Cells," *PLoS One 10*, 1.
Yang, C. et al. (2014) "Mechanical memory and dosing influence stem cell fate," *Nature Materials 13*(6), 645-652.

* cited by examiner

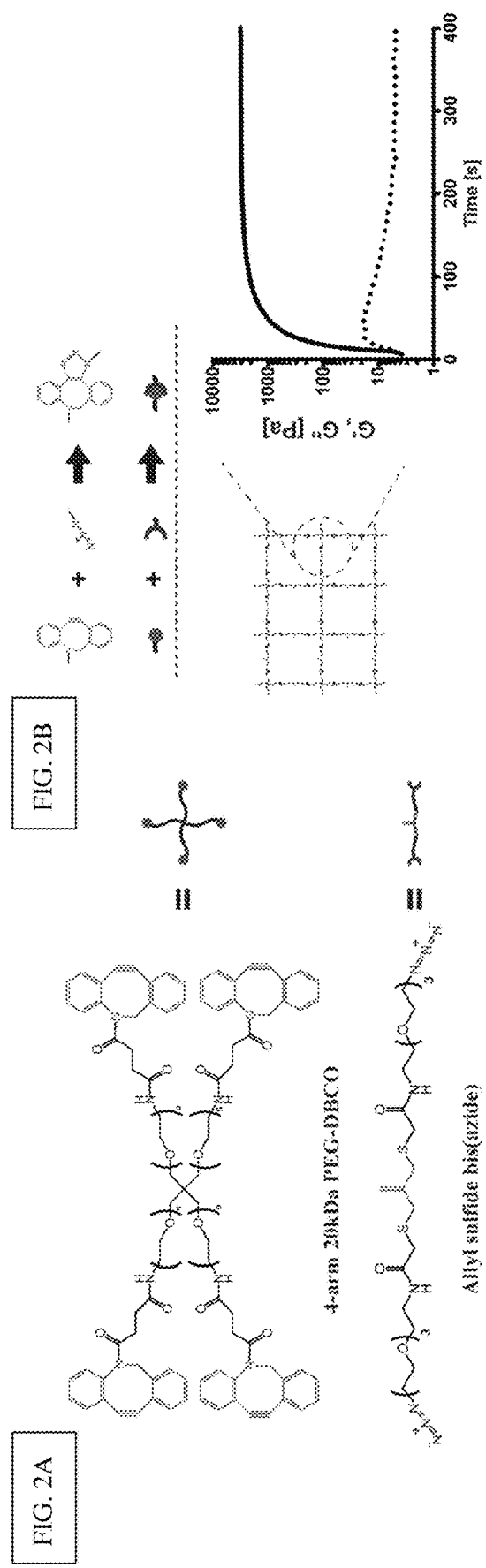

AMPLIFIED PHOTODEGRADATION OF HYDROGELS AND METHODS OF PRODUCING THE SAME

CROSS-REFERENCE TO RELATED APPLICATIONS

The present application claims the benefit of U.S. Provisional Patent Application No. 62/520,255, filed on Jun. 15, 2017, which is incorporated herein by reference.

STATEMENT OF GOVERNMENTAL SUPPORT

This invention was made with government support under grant numbers T32 GM065103 awarded by the National Institutes of Health and DMR 1408955 awarded by the National Science Foundation. The government has certain rights in the invention.

FIELD OF THE INVENTION

This invention is in the field of synthesis and amplified photodegradation of hydrogel networks and methods of producing and using the same.

BACKGROUND OF THE INVENTION

Biological scaffolds are natural or artificial structures capable of facilitating a variety of physiological processes. Such scaffolds can be formed in situ or in vitro as prefabricated matrices defined by a specific shape or structure. These scaffolds serve multiple purposes, such as, supporting cell or tissue attachment, migration, delivery, and retention. In addition to cells and/or tissues, biological scaffolds can contain bioactive agents, pharmaceutical compounds, and/or fluids, e.g., cell growth medium. As such, biological scaffolds can be seeded with cells and cultured in vitro or directly implanted into a tissue. However, three-dimensional tissue engineering requires additional considerations relating to scaffold-tissue matrices.

Tissue engineering involves the use of biological macromolecules and living cells to develop suitable substitutes for tissue or organ replacement. In order for such complex structures to develop, however, the biological scaffolds from which they form must support cell and tissue growth that is similar to natural tissue organogenesis. Along these lines, tissue engineering applications require structures composed of varying degrees of thickness and size, which can affect tissue durability. The structure and stability of newly formed tissues can vary and, for applications requiring scaffold removal, a non-disruptive separation of the scaffold-tissue complex is necessary to ensure the integrity of the tissue. Accordingly, mechanisms for severing the scaffold-tissue complex constitute an important consideration in the development of new strategies for tissue engineering. Therefore, there is a continued need for methods for the synthesis and degradation of hydrogel networks or portions therein.

SUMMARY OF THE INVENTION

This invention is in the field of synthesis and amplified photodegradation of hydrogel networks and methods of producing and using the same. This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

In one embodiment, the invention contemplates an allyl sulfide crosslinked hydrogel network. In one embodiment, said hydrogel network further comprises at least one live cell encapsulated in the network.

In one embodiment, the invention contemplates an allyl sulfide crosslinked hydrogel network, wherein said hydrogel network is in contact with a photoinitiator. In one embodiment, said photoinitiator comprises lithium phenyl-2,4,6-trimethylbenzoylphosphinate. In one embodiment, said hydrogel network further comprises at least one live cell encapsulated in said network. It is not intended that the current invention be limited to any particular photoinitiator.

It is not intended that the crosslinked hydrogel network of current invention be limited to strain-promoted azide-alkyne cycloaddition (SPAAC) crosslinking mechanisms for hydrogel networks. The present invention contemplates an allyl sulfide containing molecule crosslinked by any reaction. Other reactions, strategies, or chemistries used to create or types of crosslinked hydrogel networks include using biocompatible click chemistries (including, but not limited to: thiol-Michael additions, 1,3-dipolar cycloadditions (beyond SPAAC), oxime/hydrazone bonds, Diels Alder reactions, and radical thiol-ene and thiol-yne photopolymerizations); the reaction of amines (e.g. lysine residues) with N-hydroxysuccinimidyl esters; attachment of a peptide recognition sequence to allow for enzymatic crosslinking (for example by transglutaminase); forming the crosslinked network by associating interactions such as hydrogen bonding (or DNA complexation), or hydrophobic/ionic/host-guest interactions.

In one embodiment, the invention contemplates an allyl sulfide crosslinked hydrogel network. In one embodiment, said crosslinked hydrogel network comprises a strain-promoted azide-alkyne cycloaddition (SPAAC) hydrogel network. In one embodiment, said hydrogel network produced by a reaction between a plurality of tetrafunctional poly (ethylene glycol) dibenzocyclooctyne (PEG-DBCO) molecules and a plurality of allyl sulfide poly(ethylene glycol) (PEG-$N_3$) molecules. In one embodiment, said allyl sulfide poly(ethylene glycol) comprises allyl sulfide bis-($PEG_3$-azide). In one embodiment, said hydrogel network further comprises at least one live cell encapsulated in the network.

In one embodiment, the invention contemplates an allyl sulfide crosslinked hydrogel network, wherein said hydrogel network is in contact with a photoinitiator. In one embodiment, said crosslinked hydrogel network comprises a strain-promoted azide-alkyne cycloaddition (SPAAC) hydrogel network. In one embodiment, said photoinitiator is in solution and at least part of said network is submerged in said solution. In one embodiment, said solution further comprises a free monothiol. In one embodiment, said free monothiol comprises mPEG-SH In one embodiment, said hydrogel network comprises a network reaction between a plurality of tetrafunctional poly(ethylene glycol) dibenzocyclooctyne (PEG-DBCO) molecules and a plurality of allyl sulfide poly(ethylene glycol) (PEG-$N_3$) molecules. In one embodiment, said allyl sulfide poly(ethylene glycol) comprises allyl sulfide bis-(PEG$_3$-azide). In one embodiment, said photoinitiator comprises lithium phenyl-2,4,6-tri-methylbenzoylphosphinate. In one embodiment, said hydrogel network further comprises at least one live cell encapsulated in said network.

In one embodiment, the invention contemplates a hydrogel network wound dressing comprising an allyl sulfide crosslinked hydrogel network. In one embodiment, said crosslinked hydrogel network comprises a strain-promoted azide-alkyne cycloaddition (SPAAC) hydrogel network.

In one embodiment, the invention contemplates a composition comprising a population of cells encapsulated within a hydrogel network crosslinked with allyl sulfide or other addition fragmentation-chain transfer agent. In one embodiment, said crosslinked hydrogel network comprises a strain-promoted azide-alkyne cycloaddition (SPAAC) hydrogel network. In one embodiment, said crosslinked hydrogel network comprises crosslinks by Michael addition. In one embodiment, said crosslinked hydrogel network comprises crosslinks by thiol-ene addition. In one embodiment, said crosslinked hydrogel network comprises crosslinks by tetrazine-norbornene addition. In one embodiment, said crosslinked hydrogel network comprises crosslinks by other known means of chemical crosslinks. In one embodiment, said crosslinked hydrogel network comprises crosslinks such as cross-linked hydrogel for pharmaceutical applications described by Parhi [1]. In one embodiment, addition fragmentation chain transfer agents comprise reversible addition-fragmentation chain-transfer agents. In one embodiment, other addition fragmentation chain transfer agents include but are not limited to 2-substituted-1-propenyl compounds and thiocarbonylthio compounds. In one embodiment, said cells are live cells. In one embodiment, said cells are primary cells. In one embodiment, said cells are human cells.

In one embodiment, the invention contemplates a composition comprising a population of cells encapsulated within an allyl sulfide crosslinked hydrogel network. In one embodiment, said crosslinked hydrogel network comprises a strain-promoted azide-alkyne cycloaddition (SPAAC) hydrogel network. In one embodiment, said cells are live cells. In one embodiment, said cells are primary cells. In one embodiment, said cells are human cells.

In one embodiment, the invention contemplates a method of producing an allyl sulfide crosslinked strain-promoted azide-alkyne cycloaddition (SPAAC) hydrogel network, comprising: a) providing, i) a plurality of tetrafunctional poly(ethylene glycol) dibenzocyclooctyne (PEG-DBCO) molecules, ii) a plurality of allyl sulfide poly(ethylene glycol) (PEG-$N_3$) molecules, and b) mixing said PEG-DBCO molecules and said allyl sulfide poly(ethylene glycol) (PEG-$N_3$) molecules. In one embodiment, said allyl sulfide poly(ethylene glycol) (PEG-$N_3$) molecules are in excess, under conditions such that a hydrogel network is produced. In one embodiment, said allyl sulfide poly(ethylene glycol) comprises allyl sulfide bis-(PEG$_3$-azide). In one embodiment, further provides a step c) centrifuging said mixture. In one embodiment, further provides a step d) exposing said hydrogel network to a solution comprising a photoinitiator and a compound having a free monofunctional thiol group. In one embodiment, said photoinitiator comprises lithium phenyl-2,4,6-tri-methylbenzoylphosphinate. In one embodiment, said compound having a free monofunctional thiol group. In one embodiment, said free monofunctional thiol comprises mPEG-SH. In one embodiment, further provides a step e) exposing said hydrogel network in said solution to light under conditions wherein at least a portion of said hydrogel network is degraded. In one embodiment, said conditions include variations of light intensity, duration of exposure, etc. In one embodiment, said light comprises 350-420 nm light.

In one embodiment, the invention contemplates a method of producing an allyl sulfide crosslinked strain-promoted azide-alkyne cycloaddition (SPAAC) hydrogel network, comprising: a) providing, i) a plurality of tetrafunctional poly(ethylene glycol) dibenzocyclooctyne (PEG-DBCO) molecules, ii) a plurality of allyl sulfide poly(ethylene glycol) (PEG-$N_3$) molecules, iii) live cells, and b) mixing said PEG-DBCO molecules, said allyl sulfide poly(ethylene glycol) (PEG-$N_3$) molecules, and said live cells under conditions such that a hydrogel network is produced and at least a portion of said cells are encapsulated. In one embodiment, wherein said allyl sulfide poly(ethylene glycol) (PEG-$N_3$) molecules are in excess. In one embodiment, said allyl sulfide poly(ethylene glycol) comprises allyl sulfide bis-(PEG$_3$-azide). In one embodiment, further comprising a step c) centrifuging said mixture. In one embodiment, further comprising a step d) exposing said hydrogel network to a solution comprising a photoinitiator and a compound having a free monofunctional thiol group. In one embodiment, said photoinitiator comprises lithium phenyl-2,4,6-tri-methylbenzoylphosphinate. In one embodiment, said compound having a free monofunctional thiol group comprises methoxy-PEG-thiol. In one embodiment, further comprising a step e) exposing said hydrogel network in said solution to light under conditions wherein at least a portion of said hydrogel network is degraded. In one embodiment, said conditions include variations of light intensity, duration of exposure, etc. In one embodiment, said light comprises 350-420 nm light. In one embodiment, during said degrading at least one live cell released from said hydrogel network. In one embodiment, said cells are primary cells. In one embodiment, said cells are human cells.

In one embodiment, the invention contemplates a method of treating a patient with a wound comprising: a) providing: i) a patient with a wound, ii) an allyl sulfide crosslinked strain-promoted azide-alkyne cycloaddition (SPAAC) hydrogel network wound dressing, b) applying said wound dressing to said wound. In one embodiment, further comprising a step c) exposing said hydrogel network to a solution comprising a photoinitiator and a compound having a free monofunctional thiol group. In one embodiment, said photoinitiator comprises lithium phenyl-2,4,6-tri-methylbenzoylphosphinate. In one embodiment, said compound having a free monofunctional thiol group. In one embodiment, said free monofunctional thiol comprises mPEG-SH. In one embodiment, further comprising a step d) exposing said hydrogel network in said solution to light under conditions wherein at least a portion of said hydrogel network is degraded. In one embodiment, said light comprises 350-420 nm light. In one embodiment, said hydrogel network further comprises encapsulated live cells. In one embodiment, during said degrading at least one live cell released from said hydrogel network. In one embodiment, said wound dressing is released from said patient.

In one embodiment, the invention contemplates a method of degrading a hydrogel via a radical addition-fragmentation chain transfer (AFCT) process.

In one embodiment, the invention contemplates a method of incorporating the allyl sulfide moiety into the network backbone either through 1) a radical process or via 2) an orthogonal reaction such as strain-promoted azide-alkyne cycloaddition (SPAAC).

In one embodiment, exposure to light in the presence of a photoinitiator and a monofunctional thiol causes the cross-linked system to revert to soluble branched macromers this system could be adapted for a wide range of existing AFCT agents (beyond allyl sulfides).

In one embodiment, cells are released from the material at a user-defined time point for further analysis of intracellular protein and mRNA production as well as fluorescently activated cell sorting (FACS) wound healing application, where the hydrogel could initially serve as a protective barrier and then could be rapidly removed on-demand with a low light dose.

In some embodiments, it is desirable that cells are evenly distributed throughout a hydrogel. Even distribution can help provide more uniform tissue-like hydrogels that provide a more uniform environment for encapsulated cells. In some embodiments, cells are located on the surface of a hydrogel. In some embodiments, cells are located in the interior of a hydrogel. In some embodiments, the conditions under which cells are encapsulated within hydrogels are altered in order to maximize cell viability.

Those skilled in the art will recognize that the cells listed herein represent an exemplary, not comprehensive, list of cells that can be encapsulated within a precursor solution (and, therefore, eventually in a hydrogel) in accordance with the present invention.

In some embodiments, it is desirable that cells are evenly distributed throughout a hydrogel. Even distribution can help provide more uniform tissue-like hydrogels that provide a more uniform environment for encapsulated cells. In some embodiments, cells are located on the surface of a hydrogel. In some embodiments, cells are located in the interior of a hydrogel. In some embodiments, cells are layered within a hydrogel. In some embodiments, each cell layer within a hydrogel contains different cell types. In some embodiments, cell layers within a hydrogel alternate between two cell types.

In some embodiments, the conditions under which cells are encapsulated within hydrogels are altered in order to maximize cell viability. In some embodiments, for example, cell viability increases with lower polymer concentrations, lower photoinitiator concentration, and shorter UV exposure times. In some embodiments, cells located at the periphery of a hydrogel tend to have decreased viability relative to cells that are fully-encapsulated within the hydrogel. In some embodiments, conditions (e.g. pH, ionic strength, nutrient availability, temperature, oxygen availability, osmolarity, etc.) of the surrounding environment may need to be regulated and/or altered to maximize cell viability.

In some embodiments, cell viability can be measured by monitoring one of many indicators of cell viability. In some embodiments, indicators of cell viability include, but are not limited to, intracellular esterase activity, plasma membrane integrity, metabolic activity, gene expression, and protein expression. To give but one example, when cells are exposed to a fluorogenic esterase substrate (e.g. calcein AM), live cells fluoresce green as a result of intracellular esterase activity that hydrolyzes the esterase substrate to a green fluorescent product. To give another example, when cells are exposed to a fluorescent nucleic acid stain (e.g. ethidium homodimer-1), dead cells fluoresce red because their plasma membranes are compromised and, therefore, permeable to the high-affinity nucleic acid stain.

In general, the percent of cells in a precursor solution is a percent that allows for the formation of hydrogels in accordance with the present invention. In some embodiments, the percent of cells in a precursor solution that is suitable for forming hydrogels in accordance with the present invention ranges between about 0.1% w/w and about 80% w/w, between about 1.0% w/w and about 50% w/w, between about 1.0% w/w and about 40% w/w, between about 1.0% w/w and about 30% w/w, between about 1.0% w/w and about 20% w/w, between about 1.0% w/w and about 10% w/w, between about 5.0% w/w and about 20% w/w, or between about 5.0% w/w and about 10% w/w. In some embodiments, the percent of cells in a precursor solution that is suitable for forming hydrogels in accordance with the present invention is approximately 5% w/w. In some embodiments, the concentration of cells in a precursor solution that is suitable for forming hydrogels in accordance with the invention ranges between about $1 \times 10^5$ cells/ml and $1 \times 10^8$ cells/ml or between about $1 \times 10^6$ cells/ml and $1 \times 10^7$ cells/ml.

In some embodiments, a single hydrogel comprises a population of identical cells and/or cell types. In some embodiments, a single hydrogel comprises a population of cells and/or cell types that are not identical. In some embodiments, a single hydrogel may comprise at least two different types of cells. In some embodiments, a single hydrogel may comprise 3, 4, 5, 10, or more types of cells. To give but one example, in some embodiments, a single hydrogel may comprise only embryonic stem cells. In some embodiments, a single hydrogel may comprise both embryonic stem cells and hematopoietic stem cells. In some embodiments, the hydrogel may contain mesenchymal stem cells.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "biocompatible polymer" refers to a synthetic or natural material that is, for example, non-toxic to biological systems and/or congruent with biological processes. In this respect, biocompatibility of polymer materials denote minimal, negligible, or no risk of immunorejection, injury, damage and/or toxicity to living cells, tissues, organs, and/or biological systems. In illustrative embodiments, the biocompatible polymer is also biodegradable and/or susceptible to saccharide degradation. In illustrative embodiments, the biocompatible polymer is, for example, but not limited to, polyvinyl alcohol (PVA), polylactic acid (PLA), polyglycolic acid (PGA), poly(lactide-co-glycolide) (PLGA) and/or poly(L-lactide) (PLLA), and the like.

As used herein, the term "biodegradable" or "biodegradation" refers generally to the decomposition, i.e., breaking down, of materials, such as, for example, biological or natural material, organic matter, biocompatible materials, biocompatible polymers, and/or biosynthetic materials, when exposed to a biodegradative agent. In illustrative embodiments, "biodegradation" includes, but, is not limited to, biolytic degradation, proteolytic degradation, lipolytic degradation, saccharide degradation, degradation by microorganisms, such as, e.g., bacteria, fungi, viruses, and the like, and degradation by other natural or synthetic processes that are compatible with one or more biological systems or environments.

As used herein, the terms "extracellular matrix" or "ECM," are used interchangeably, and encompass various liquid, gelatinous, semi-solid, or solid protein mixtures congruent with the complex extracellular environment found in many tissues. The extracellular matrix may be employed as a substrate for cell and tissue culture preparations or as a surface for cell adhesion to a hydrogel matrix. The "extracellular matrix" may also include basement membrane extract and/or Engelbreth-Holm-Swarm (EHS) matrix. In illustrative embodiments, Matrigel™ (BD Biosciences, Franklin Lakes, N.J.) is employed as the EMC, when necessary for particular applications.

As used herein, the terms "hydrogel" or "hydrogel matrix" are used interchangeably, and encompass polymer and non-polymer based hydrogels. "Hydrogel" is also meant to refer to all other hydrogel compositions disclosed herein, including hydrogels that contain polymers, copolymers, terpolymer, and complexed polymer hydrogels, i.e., hydrogels that contain one, two, three, four or more monomeric or multimeric constituent units. Along the same lines, the terms "tissue hydrogel" or "tissue matrix" refer to any composition formed into a porous matrix into which cells or tissue can grow in three dimensions. Hydrogels are typically continuous networks of hydrophilic polymers that absorb water.

As used herein, the term "organ" refers to a part or structure of the body, which is adapted for a special function or functions, and includes, but is not limited to, the skin, the lungs, the liver, the kidneys, and the bowel, including the stomach and intestines. In particular, it is contemplated that organs which are particularly susceptible to dysfunction and failure arising from an injury are amendable to tissue-engineered reconstruction and are encompassed by the term "organ."

As used herein, the term "polymer" refers to a macromolecule made of repeating monomer or multimer units. Polymers of the present disclosure, include, but are not limited to, poly(hyaluronic acid), poly(sodium alginate), poly(ethylene glycol) (PEG), poly(lactic acid) polymers, poly(glycolic acid) polymers, poly(lactide-co-glycolides) (PLGA), poly(urethanes), poly(siloxanes) or silicones, poly (ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(methacrylic acid), polylactic acid (PLA), poly(L-lactide) (PLLA), polyglycolic acids (PGA), nylons, polyamides, polyanhydrides, poly(ethylene-co-vinyl alcohol) (EVOH), polycaprolactone, polyvinylhydroxide, poly(ethylene oxide) (PEO), and polyorthoesters or a copolymer or terpolymer formed from at least two or three members of the groups, respectively. The terms "hydrogel polymers" or "matrix polymer materials" refer to the materials used to make the hydrogels of the present disclosure. The terms refer to both monomeric units of the materials and the polymers or co-polymers made therefrom. Individual matrix units (monomers) or polymers can be biocompatible, biodegradable, saccharide biodegradable and/or non-biodegradable.

As used herein, the terms "saccharide degradation" or "saccharide biodegradation" or "saccharide biodegradable" refer to the decomposition, i.e., breaking down, of materials such as, for example, biocompatible polymers, co-polymers, terpolymers, and the like, when exposed to a saccharide solution. In illustrative embodiments, biocompatible polymers are susceptible to saccharide degradation by, for example, saccharide catalyzed displacement, competitive binding of saccharides, and/or sequestration of polymer units via saccharide interaction, and the like. In illustrative embodiments, the saccharides are monosaccharides, disaccharides, oligosaccharides, or polysaccharides, and the like, that bind polymers such as, for example, phenylboronate-containing copolymers (PCCs), with increased affinity compared to other PCC-polymer intermolecular interactions, e.g., PVA-PCC. The rate of degradation may be fast, e.g., degradation may take place in minutes, or slow, e.g., degradation may take place over hours, days, weeks or months, or the polymer may degrade in response to a particular saccharide concentration. In illustrative embodiments, the rate of degradation can be controlled by the type of saccharide and/or polymer that is used.

As used herein, the terms "scaffolding polymers" or "scaffolding materials" refer to the materials used to generate hydrogel scaffolds. The terms refer to both monomeric units of the materials and the polymers made therefrom. Individual scaffolding units (monomers) or polymers can be biocompatible, biodegradable, saccharide biodegradable, and/or non biodegradable.

As used herein, the term "tissue" or "tissues" refer to singular or multiply-layered structures, e.g., monolayers or stratified layers of cells, which typically constitute organ constituents. One or more different tissues may form an organ or organs. An organ may also be composed of only one type of tissue or cell. In illustrative embodiments, "tissue," for example, emanates from one or more various types of cell layers. In this regard, tissues are composed of, for example, one or more cell-types, which include, but are not limited to, cells, muscle cells, epithelial cells, endothelia cells, stem cells, umbilical vessel cells, corneal cells, cardiomyocytes, aortic cells, corneal epithelial cells, aortic endothelial cells, fibroblasts, hair cells, keratinocytes, melanocytes, adipose cells, bone cells, osteoblasts, airway cells, microvascular cells, mammary cells, vascular cells, chondrocytes, and/or placental cells, and the like.

As used herein, microgel particles referred to as "$10^2$ μm microgels" or "100 μm microgels" refer to microgel particles ranging between 30 μm to 350 μm, with mean particle diameters of 120±60 μm and 130±80 μm for gels containing excess DBCO or azide groups, respectively. In some embodiments, particles of this $10^2$ μm microgels size range are created when component hydrogel solutions are vortexed.

As used herein, microgel particles referred to as "$10^1$ μm microgels" or "10 μm microgels" refer to microgel particles ranging with average particle diameter sizes of 16±6 μm and 15±5 μm for DBCO and azide gels, respectively. In some embodiments, particles of this $10^1$ μm microgel particle size range are created when component hydrogel solutions are sonicated.

As used herein, the term "live cell" is not to be limited to when every single cell is viable, but wherein a significant portion of cell population is viable. In some embodiments, live cell comprises greater than 50% viability. In some embodiments, live cell comprises greater than 80% viability. In some embodiments, live cell comprises greater than 90% viability. In preferred embodiments, live cell comprises greater than 95% viability.

As used herein, the term "viability" is not just if a population is alive or not, but can be distinguished from the all-or-nothing states of life and death by use of a quantifiable index between 0 and 1 (or 0% and 100%).

As used herein, the term "click chemistry" or more commonly called tagging, refers to a class of biocompatible reactions intended primarily to join substrates of choice with specific biomolecules. Click chemistry is not a single specific reaction, but describes a way of generating products that follow examples in nature, which also generates substances by joining small modular units. In general, click reactions usually join a biomolecule and a reporter molecule. Click chemistry is not limited to biological conditions: the concept of a "click" reaction has been used in pharmacological and various biomimetic applications. However, they have been made notably useful in the detection, localization and qualification of biomolecules. Examples of click reactions are selected from the group consisting of thiol-ene chemistry, Michael type additions, copper-click azide alkyne chemistries, strain-promoted alkyne-azide cycloadditions (SPAAC) chemistry, and Diels Alder type reactions (such as Norbornene: Tetrazine reactions)

As used herein, the term "complementary clickable reactive groups" refers to types of reactive groups that react in "click chemistry." Non-limiting examples of "complementary clickable reactive groups" include i) azide group and strained alkyne group; ii) nitrone group and a cyclooctyne group; iii) using a nitrile oxide group (as a 1,3-dipole) and a norbornene group (as a dipolarophile); iv) oxanorbornadiene group and an azide group; v) trans-cyclooctene group and an s-tetrazine group; and vi) tertiary amine or isocyanopropanoate groups and an s-tetrazine group.

As used herein, the term "Chain-transfer agent" refers to a substance able to react with a chain carrier by a reaction in which the original chain carrier is deactivated and a new chain carrier is generated [2].

As used herein, the term "chain transfer" refers to a type of polymerization reaction by which the activity of a growing polymer chain is transferred to another molecule.

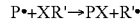

Chain transfer reactions reduce the average molecular weight of the final polymer. Chain transfer can be either introduced deliberately into a polymerization (by use of a chain transfer agent) or it may be an unavoidable side-reaction with various components of the polymerization. Chain transfer reactions occur in most forms of addition polymerization including radical polymerization, ring-opening polymerization, coordination polymerization, and cationic as well as anionic addition polymerization.

As used herein, the term "complementary clickable reactive surface groups" refers to having on the surface of a microgel at least one complementary clickable reactive group, as described above. Such groups may react with the complementary group to link microgels.

As used herein, the term "photoinitiator" refers to a compound that undergoes a photoreaction on absorption of light (including UV or visible), producing reactive species (free radicals, cations or anions). These are capable of initiating or catalyzing chemical reactions that result in significant changes in the solubility and physical properties of suitable formulations.

Tissue Engineering Scaffolds

Hydrogel matrices can be used as conformable, malleable, or injectable conduits for in situ or in vivo administration of cells, drugs, or tissues to a subject. Hydrogels also function as scaffolds that facilitate in vitro and ex vivo cell growth, thereby allowing for cell-sheet and/or tissue formation prior to, or simultaneous with, administration to a subject. Synthetic hydrogels can be sterilized and do not have the associated risk of harboring contaminants, e.g., infectious agents. However, synthetic hydrogels typically do not mimic the extracellular matrix (ECM) and therefore may not properly direct cellular ingrowth or function. Hydrogels composed of an ECM imitate the native cellular environment. However, unless such hydrogels are made from autologous material, i.e., recognized as "self" by the immune system, immunorejection is possible.

Moreover, removal of the supporting matrix on which the cells or tissue constructs grow may be required for complete tissue reconstruction. Separation of the hydrogel matrix from tissue that has formed therewith typically disrupts ECM and cellular junctions of the tissue. Accordingly, tissue engineering is enhanced by the manufacture of biodegradable scaffolds that allow for in vitro, ex vivo, in vivo, or in situ confluent cell growth, such that cells, cell-sheets, and/or tissue constructs can be harvested in a non-invasive manner, e.g., by saccharide biodegradation and/or without the use of proteolytic enzymes. In this respect, the present disclosure advantageously provides hydrogel scaffolds, wherein cells, cell-sheets, and/or tissues are grown and harvested as contiguous cell-layers with intact cell-cell junctions and deposited ECM.

The harvested cells, cell-sheets, and/or tissues can be applied to various cell or tissue reconstruction applications, including, but not limited to, cell and tissue grafting, skin-grafting, allografting, wound healing grafts, aesthetic or functional re-modeling grafts, skin replacement, ocular reconstruction, liver tissue reconstruction, cardiac patching, bladder augmentation, ligament cell sheet patching, bone tissue repair and reconstruction, cartilage tissue repair and reconstruction, vasculature repair and reconstruction, thyroid tissue reconstruction, esophageal ulcer patching, neuronal tissue repair, pancreatic tissue repair, and tracheal reconstruction. Furthermore, in vitro cell culturing supports cell adhesion, cell viability, and cell proliferation on the hydrogel scaffolds disclosed herein, which, for example, demonstrates their general biocompatibility.

The biocompatibility of the hydrogel scaffolds emanate at least partially from the mild synthesis procedures described herein, which do not involve the use of harsh chemicals and/or gelation techniques. In addition, the hydrogel scaffolds possess monosaccharide inducible gel-sol phase transformability. As such, the hydrogel scaffolds are suitable for cell-sheet and tissue engineering, as well as cell immobilized applications relating thereto. The hydrogel scaffolds can be applied for immobilizing various types of mammalian cells, including but not limited to, hybridoma cells, kidney cells, Chinese hamster ovaries (CHO) cells, pancreatic islets, corneal epithelial cells, fibroblasts, chondrocytes, articular chondrocytes, neuroblasts, vascular endothelial cells, hepatocytes, esophageal epithelial cells, and erythrocytes. The immobilization can be achieved through various procedures, including but not limited to, adhesion, matrix entrapment, and microencapsulation. Hydrogels are typically composed of various monomeric constituents, and polymers, copolymers, or terpolymers thereof.

Polymer hydrogels are suitable matrix materials because they can be readily manufactured with a wide range of reproducible properties and structures. Depending on their composition, polymer matrices provide varying degrees of mechanical support for withstanding compressive and/or tensile forces. In this regard, maintaining the shape and integrity of the matrix can be important for certain tissue engineering applications, such as implanting newly formed tissue or a tissue-matrix complex into a subject. Typical tissue-matrix structures include various types of polymer hydrogels, which differ in their susceptibility to biodegradation.

The morphology of a hydrogel scaffold may also influence the development of tissue structure. The size, shape, and vascularization of various tissues, moreover, impart their functional characteristics within a biological system. Accordingly, it is important to properly design hydrogel scaffolds to facilitate a suitable range of mechanical and biological functions. Synthetic polymeric materials can be precisely controlled in material properties, quality, and mode of manufacture. Further, the present disclosure enables the production of synthetic polymers by various techniques, thereby providing for a consistent supply of such hydrogels in large quantities. The mechanical and physical properties of synthetic polymers can be readily adjusted through variation of molecular structures so as to fulfill their functions without the use of either fillers or additives.

A variety of polymers can be utilized to fabricate hydrogel matrices for cell-sheet and tissue production. These materials are typically employed as structural elements in the hydrogel, and include, but are not limited to, poly(hyaluronic acid), poly(sodium alginate), poly(ethylene glycol) (PEG), poly(lactic acid) polymers, poly(glycolic acid) polymers, poly(lactide-co-glycolides) (PLGA), poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(methacrylic acid), polylactic acid (PLA), poly(L-lactide) (PLLA), polyglycolic acids (PGA), nylons, polyamides, polyanhydrides, poly(ethylene-co-vinyl alcohol) (EVOH), polycaprolactone, polyvinylhydroxide, poly(ethylene oxide) (PEO). Some of these polymers are extensively used in biomedical applications such as drug delivery and are FDA approved for a variety of applications. A number of biocompatible polymers, such as, e.g., PVA, PGA, PLA, PLLA, PLGA, and other synthetic polymer tissue matrices are also known in the art.

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIGS. 2A&B show the network structure of AFCT-based photodegradable hydrogels. FIG. 2A shows chemical structures of cyclooctyne-terminated PEG macromer and azide crosslinker containing the allyl sulfide functionality. FIG. 2B shows that upon mixing the two species, a hydrogel network is rapidly formed incorporating the allyl sulfide reactive groups. Gelation is monitored by shear rheology in situ, and the storage modulus (solid line) and loss modulus (dotted line) are tracked. The final elastic modulus is reached within 10 min.

FIG. 4A shows the Effect of photoinitiator concentration. Hydrogels were swollen with 25×10$^{-3}$ in mPEG-SH and 1×10$^{-3}$ m (♦), 2×10$^{-3}$ m (●), 4×10$^{-3}$ m (■) or 8×10$^{-3}$ m (▲) LAP. b) Effect of light intensity. Hydrogels swollen with 4×10$^{-3}$ m LAP and 25×10$^{-3}$ m mPEG-SH and exposed to 2 (✦), 10 (✧) or 40 (Δ) mW cm$^{-2}$ 365 nm light. FIG. 4C shows the apparent rate constants for photodegradation are plotted as a function of light intensity, yielding a straight line with slope $k_{app}$/l0×10$^4$ of 235 cm$^3$ mW$^{-1}$ s$^{-1}$.

FIG. 5A shows A 1 cm thick hydrogel containing 4×10$^{-3}$ m LAP and 25×10$^{-3}$ m mPEG-SH was irradiated with 10 mW cm-2 365 nm light, and completed eroded over the course of ≈1 min. In this optically thick gel, 87% of the incident light is attenuated through the sample (i.e., only 13% of the light reaches the bottom of the sample). Macroscopic images of the gel are shown at 0, 20, 44, and 74 s (left to right, top to bottom). Scale bar: 5 mm. FIG. 5B shows cells that were both encapsulated for 24 h and subsequently released remained highly viable. Top panel: hMSCs 24 h after encapsulation are 90% viable. Bottom panel: released cells remain viable and spread on glass coverslips over 24 h. Cells were stained with calcein AM (green, live) and ethidium homodimer (red, dead). Scale bar: 100 µm (top panel) and 300 µm (bottom panel). FIG. 5C A 150 µm thick cell-laden hydrogel was selectively exposed to light (365 nm at 10 mW cm$^{-2}$) for 1 min through a photomask to induce spatially controlled photodegradation and release of a subset of the encapsulated cells. Cells remaining in hydrogel monoliths stained with calcein AM (green) and ethidium homodimer (red). Scale bar: 100 µm.

FIG. 6A in the left panel shows the concentration profile of mPEG-SH within a 260 µm thick hydrogel over a 5 min swell time of a mPEG-SH bath placed on the top of the hydrogel. The right panel shows the concentration profile throughout the gel has nearly reached the concentration of the bulk solution after 5 min.

DETAILED DESCRIPTION OF THE INVENTION

Figure 1:
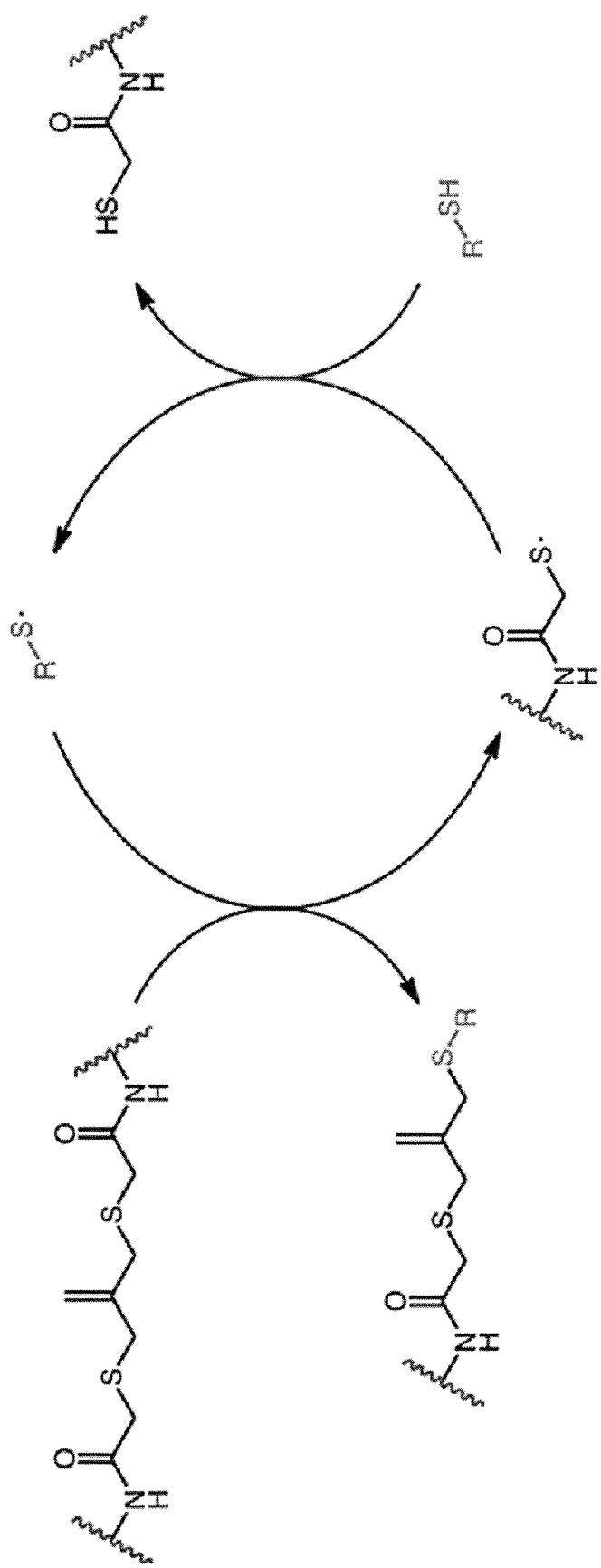
FIG. 1 shows the amplification of photodegradation by chain transfer. Addition-fragmentation chain transfer (AFCT) crosslinks exposed to a photogenerated monothiyl radical (red) transition from a crosslinked state to a non-crosslinked state and also regenerate a monothiyl radical capable of additional crosslink fragmentation reactions.

This invention is in the field of synthesis and amplified photodegradation of hydrogels and methods of producing and using the same. Hydrogels synthesized from crosslinking reactions between water soluble macromolecular precursors are widely used in a number of biomaterials applications, for example as drug or cell delivery vehicles and as cell culture scaffolds. Many of the bio-click reactions used to form hydrogels allows direct encapsulation of biologics and cells, while maintaining their activity and viability, respectively. Furthermore, many techniques exploit the ability to create multifunctional hydrogel systems with spatiotemporally controlled material properties, biological functionalities, and printed cell structures. Along with this complexity, researchers have been further interested in methods to better characterize these complex systems, control their properties on demand, and temporally tune properties such as degradation or viscoelasticity.

With respect to temporally controlling hydrogel properties, many regenerative medicine applications that embed cells in hydrogels require degradation of the network structure to allow formation of focal adhesions, proliferation, migration, deposition of matrix components, and even to avoid fibrotic encapsulation of the implanted biomaterials. Hydrogels are routinely degraded by hydrolytic, enzymatic, or photolytic mechanisms, and each mechanism provides specific advantages. More recently, hydrogels with photo-cleavable crosslinks have been developed that allow spatiotemporal control of the degradation process. Spatiotemporal control of degradation has found numerous applications in guiding cellular proliferation, migration, and differentiation. One limitation to man; of the photodegradable groups used in biomaterial applications to date, however, is that the reactions rely on "one-photon one-event" processes. A photolabile molecule incorporated directly into the polymer backbone absorbs a photon and undergoes a cleavage reaction. This subsequently requires either long exposure times or high quantum yields.

With this in mind, hydrogels are described herein that can be degraded via a radical addition-fragmentation chain transfer (AFCT) process. Allyl sulfides have been used as efficient AFCT functionalities to introduce plasticity into crosslinked networks and recently to reversibly photopattern biomolecules within a hydrogel. The allyl sulfide moiety can be incorporated into the network backbone either through a radical process or via an orthogonal reaction such as strain-promoted azide-alkyne cycloaddition (SPAAC). Subsequent exposure to light in the presence of a photoinitiator and a monofunctional thiol causes the crosslinked system to revert to soluble branched macromers. Photogenerated thiyl radicals rapidly propagate through thiol-ene addition reactions and chain transfer events. Allyl sulfide moieties in a crosslinking state participate in a reversible thiol-ene addition with non-crosslinking thiyl radicals, converting the allyl sulfides into a non-crosslinked state. Subsequent thiyl-thiol chain transfer events allow one absorbed photon to cleave multiple crosslinks, whereas current biocompatible photo-degradation strategies are limited to a maximum of one crosslink cleavage by one photon. Furthermore, the low absorptivity of the photoactive compounds in this system allow for deep penetration of light through the samples. While the primary focus is upon allyl sulfides, this system could be adapted for a wide range of existing AFCT agents.

The allyl sulfide degradable hydrogel system of the present invention is cytocompatible and may be used for many cellular applications. Cells encapsulated in the present invention degradable hydrogel system can be released from the material at a user-defined time point for further analysis of intracellular protein and mRNA production as well as fluorescently activated cell sorting (FACS). This system would also be beneficial in a wound healing application, where the hydrogel could initially serve as a protective barrier and then could be rapidly removed on-demand with a low light dose. Additionally, this material can be used for the photolithographic production of three dimensional cell laden structures and can also be used as a templating material to produce void-forming hydrogels.

Hydrogels synthesized from crosslinking reactions between water soluble macromolecular precursors are widely used in a number of biomaterials applications, for example, as drug or cell delivery vehicles and as cell culture scaffolds [3, 4]. Many of the bioclick reactions used to form hydrogels allow direct encapsulation of biologics and cells, while maintaining their activity and viability, respectively [5-9]. Furthermore, many techniques exploit the ability to create multifunctional hydrogel systems with spatiotemporally controlled material properties [10, 11], biological functionalities [9, 12, 13], and printed cell structures [14, 15]. Along with this complexity, researchers have been further interested in methods to better characterize these complex systems, control their properties on demand, and temporally tune properties such as degradation or viscoelasticity.

With respect to temporally controlling hydrogel properties, many regenerative medicine applications that embed cells in hydrogels require degradation of the network structure to allow formation of focal adhesions, proliferation, migration, deposition of matrix components, and even to avoid fibrotic encapsulation of the implanted biomaterials. Hydrogels are routinely degraded by hydrolytic [16], enzymatic [17], or photolytic mechanisms [10, 18], and each mechanism provides specific advantages. With their high water content, hydrogels with hydrolytically cleavable crosslinks typically degrade through a uniform, bulk process; whereas hydrogels that are proteolytically cleavable often degrade through a local mechanism that depends on cell-secreted enzymes. More recently, hydrogels with photocleavable crosslinks have been developed that allow spatiotemporal control of the degradation process. In one example, Kloxin et al. demonstrated on demand control of network crosslinking density and elastic modulus, and used materials with photocleavable crosslinks to study the effects of mechanical properties on the reversibility of the fibroblast-to-myofibroblast transition in heart valve cells [19]. Since these early studies, spatiotemporal control of degradation has found numerous applications in guiding cellular proliferation, migration, and differentiation [18, 20-25]. One limitation to many of the photodegradable groups used in biomaterial applications to date, however, is that the degradation relies on "one-photon one-event" reactions. A photolabile molecule, such as a nitrobenzyl or coumarin group, incorporated directly into the polymer backbone absorbs a photon and undergoes a cleavage reaction. This subsequently requires either long exposure times or high quantum yields.

With this in mind, hydrogels were synthesized that can be degraded via a radical addition-fragmentation chain transfer (AFCT) process, where a single photon initiates multiple events and amplifies the degradation process. Allyl sulfides have been used as efficient AFCT functionalities to introduce plasticity into crosslinked networks [26-28] and recently to reversibly photopattern biomolecules within a hydrogel [12]. To incorporate this moiety into biomaterial systems, a symmetric allyl sulfide crosslinker flanked with azide functionalities was synthesized for formation of a hydrogel network through a strain-promoted azide-alkyne cycloaddition (SPAAC). Subsequent exposure to light in the presence of a photoinitiator and a monofunctional thiol causes the crosslinked system to revert to soluble branched macromolecules. Upon exposure, photogenerated thiyl radicals rapidly propagate through thiol-ene addition reactions and chain transfer events (FIG. 1) [26, 27, 29]. Allyl sulfide moieties in a crosslinking state participate in a reversible thiol-ene addition with noncrosslinking thiyl radicals, converting the allyl sulfides into a non-crosslinked state and generating a thiyl radical bound to the network ("network thiyl"). Alternating cycles of thiol-ene addition and chain transfer from a liberated network thiyl to a free thiol replace crosslinking allyl sulfides with non-crosslinking counterparts. Thiyl-thiol chain transfer events allow one absorbed photon to cleave multiple crosslinks, whereas current biocompatible photodegradation strategies typically rely on mechanisms where there is a maximum of one crosslink cleavage by one photon, with typical quantum yields being much lower [30]. Moreover, a lower concentration of photoinitiator is required for radical mediated photodegradation of allyl sulfide-containing hydrogels, compared to traditional photodegradable hydrogels that have one or more photoactive constituents per crosslink. Crosslinked hydrogel networks were formed through a SPAAC reaction between a tetrafunctional poly(ethylene glycol) dibenzocyclooctyne (PEG-DBCO) and an allyl sulfide bis-(PEG3-azide) (FIG. 2A). This bio-orthogonal "click" reaction proceeds rapidly at physiological conditions, and has been used in numerous studies as a cytocompatible crosslinking strategy [18] [22][31] [32]. Specifically, a 7.5 wt % solution of PEG-DBCO ($15 \times 10^{-3}$ m DBCO) and allyl sulfide crosslinker ($16.5 \times 10^{-3}$ m azide) was polymerized in situ on a rheometer. Excess azide was chosen to ensure complete conversion of the DBCO functionalities and to avoid side reactions during the subsequent thiol-ene reactions, as strained alkynes are known to react with thiols in a Michael-type addition and also participate in thiolyne radical additions [33-39]. The gel point was estimated by the crossover of G' and G", which occurred in <30 s, while a final modulus of 3500} 660 Pa was achieved in ≈10 min for this formulation (FIG. 2B).

Figure 3A:
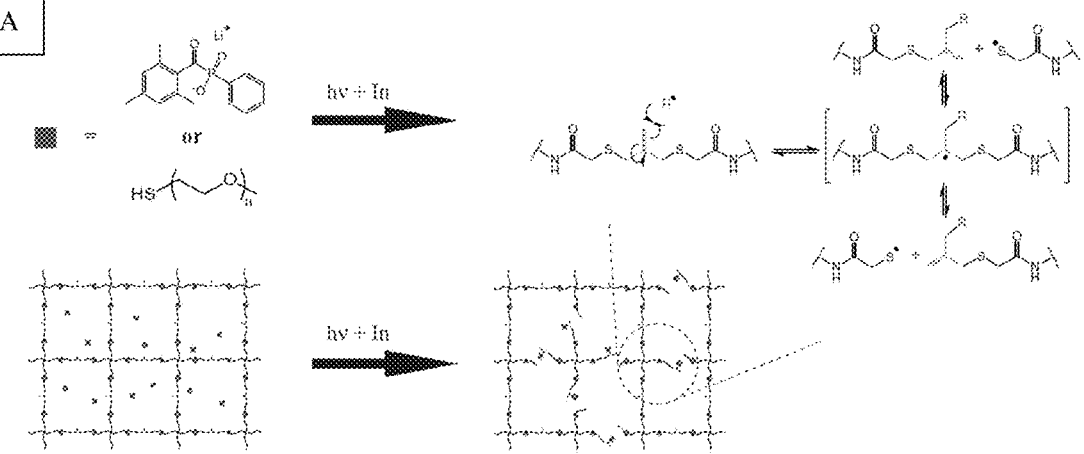
FIG. 3 A-C shows Light-triggered radical network degradation. a) Photodegradation mechanism: in the presence of LAP and mPEG-SH, crosslinking molecules are fragmented by photoinitiator radicals or non-crosslinking monothiyl species when exposed to light. b) In the absence of free mPEG-SH, incomplete photodegradation is observed. The material is exposed to 365 nm light at 10 mW cm$^{-2}$ at 30 s, and the light is shuttered for 1 min at 120 s (light exposure is indicated by purple shading). Rheological traces were performed at a frequency of 1 (black) and 10 rad s$^{-1}$ (gray), monitoring the storage (solid line) and loss (dotted line) moduli, with both normalized to the initial storage modulus. Evidence for rapid network reorganization is seen in the frequency dependence of the measurements during light exposure, while the curves converge when the light is shuttered (120-180 s) and as the photoinitiator is depleted (less than 1% LAP remains after 300 s). c) Incorporation of mPEG-SH allows controlled photodegradation of the gel and tuning of the storage modulus. mPEG-SH was swollen into the network at 0 m (♦), 5×10$^{-3}$ m (✳), 15×10$^{-3}$ m (▲), 25×10$^{-3}$ m (•), and 50×10$^{-3}$ m (●). Reverse gelation occurs when mPEG-SH concentrations of 25×10$^{-3}$ and 50×10$^{-3}$ m are used.

For subsequent photodegradation, the hydrogel was equilibrium swollen, and then placed in a solution containing varying concentrations of the photoinitiator lithium phenyl-2,4,6-trimethylbenzoylphosphinate (LAP) [40, 41] ($1 \times 10^{-3}$ to $8 \times 10^{-3}$ m) and a methoxy-PEG-thiol (mPEG-SH, Mn≈500 Da, from 0 to $50 \times 10^{-3}$ m). Exposure to light generates photoinitiator radical species, which can add directly to the olefin of the allyl sulfide or undergo chain transfer to a free thiol, which in turn reacts with the allyl sulfide (FIG. 3A). After 20 min of swelling, the gels were irradiated with 365 nm light (2-40 mW cm$^{-2}$), and the degradation was tracked via changes in the shear storage and loss moduli with exposure time.

Figure 3B:
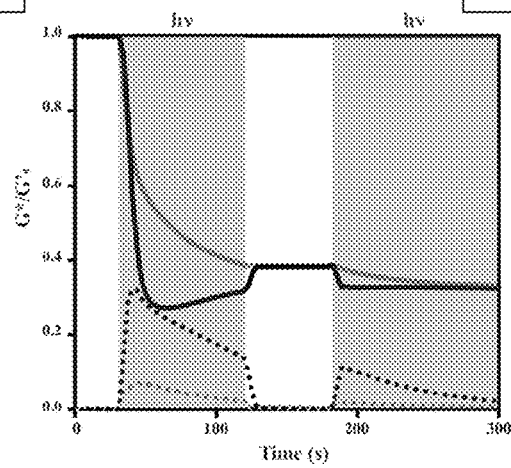

When the exchange solution contained only $4 \times 10^{-3}$ in LAP and no free thiol, significant photodegradation occurs, but not to an extent that results in reverse gelation (FIG. 3B). In this condition, there are initially no free thiols present in the hydrogel system; the only sulfur atoms are in the thioethers of the crosslinker. Thus, photodegradation is likely due to the direct addition of the photoinitiator radical fragments to the olefin of the allyl sulfide crosslinker. According to FIG. 9, this reaction generates a new olefin and also a pendant thiyl radical. In the presence of thiyl radicals, the network is expected to reorganize rapidly as the system propagates through a number of thiol-ene additions, each consuming one thiyl radical and generating another [26, 29, 42]. Evidence for this network reorganization is shown in FIG. 3B. The large increase in the loss modulus upon exposure to light indicates a significant shift the viscoelastic properties of the network from an almost purely elastic material to one that is more fluid in nature. This behavior is typical of networks that are crosslinked by dynamic linkages, such as hydrazone bonds [43, 44], host-guest interactions [14, 45], electrostatics [46-48], and others (see reviews by Kloxin and Bowman [49], Rosales and Anseth [50], and Wang and Heilshorn [51]), which display frequency dependent mechanical properties. This is further emphasized by a near crossover of G' and G", indicating that the material is approaching the reverse gel point (i.e., behaving as soluble, highly branched polymer) at the given strain rate (1 rad s$^{-1}$).

Figure 9:
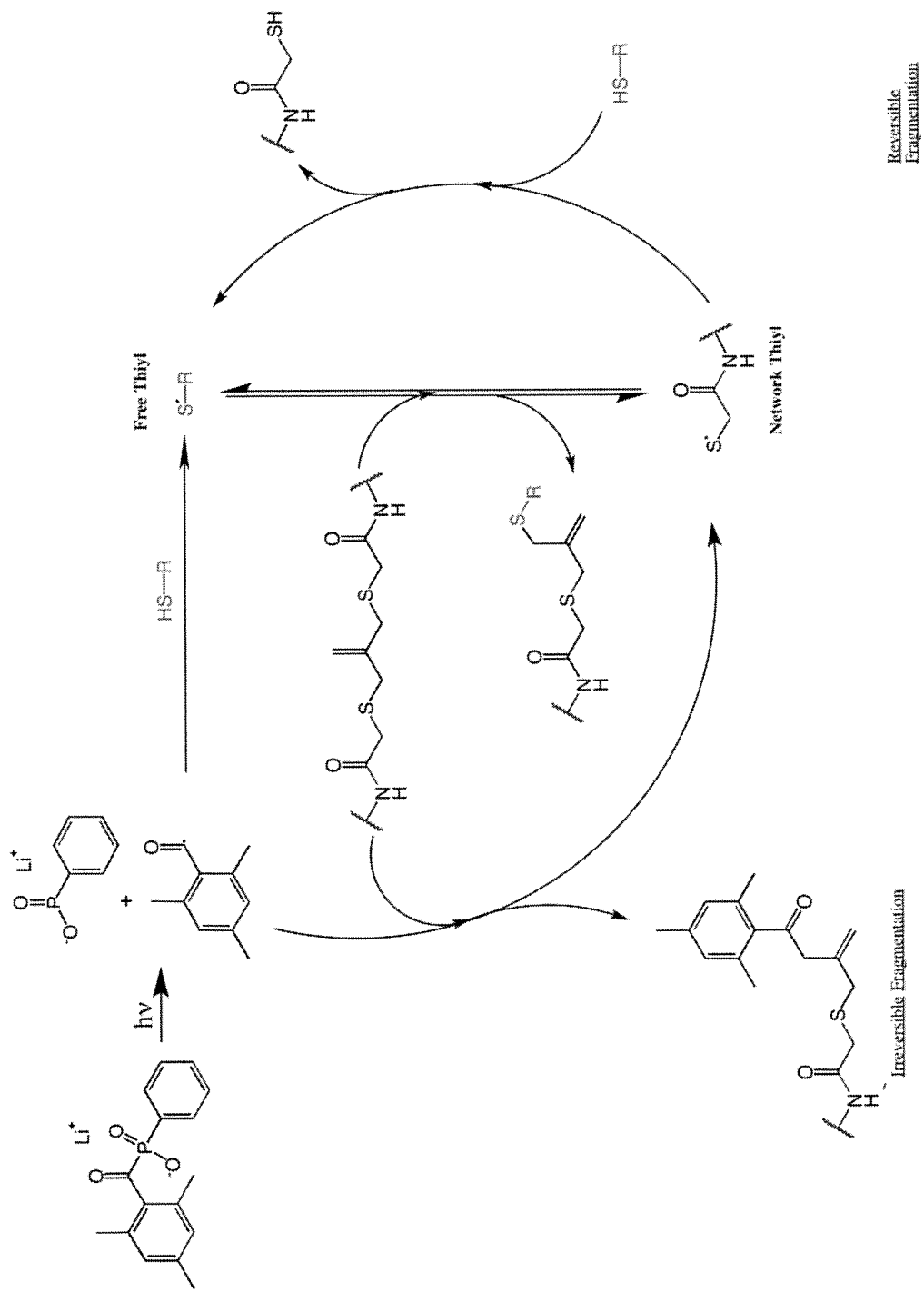
FIG. 9 show an expanded reaction scheme including addition to the olefin by initiator fragments.

An apparent anomaly is also seen in the 1 rad s$^{-1}$ rheological trace, wherein G' reaches a minimum after ≈20 s of exposure and then increases before reaching a plateau (FIG. 3B—black). This observation is likely due to a combination of photoinitiator consumption during light exposure and the generation of pendant network thiyls after allyl sulfide cleavage (FIG. 9). Initially, LAP is at its highest concentration (4×10$^{-3}$ m), leading to the highest rate of radical generation and allyl sulfide crosslink cleavage. The product of the allyl sulfide cleavage by LAP is a pendant thiyl radical. The pendant thiyl radicals have limited mobility, but are reactive toward other allyl sulfide species and can reform a crosslink upon addition to a network allyl sulfide molecule, which results in network reorganization, but not photodegradation [26]. Consequently, the measured G' during the radical mediated network reorganization is lower than the value that would be obtained without radical generation, because crosslinked strands dissipate their potential energy upon crosslink reorganization. Here, it was observed that the generation of network thiyls leads to a shift from a purely elastic network to a viscoelastic network with a frequency dependent storage and loss modulus. For comparison, the same experiment was performed at 10 rad s$^{-1}$ and the results superimposed (FIG. 3B—gray). At the higher sampling frequency, the hydrogel is less capable of dissipating the imposed force, and the storage modulus is a closer representation of what would be measured in the absence of radicals. To demonstrate the effect of network rearrangement on the storage modulus, the light was briefly shuttered at 120 s. The hydrogel subsequently reverted back to more purely elastic behavior, which led to an increase in G' and a decrease in G". At this point, the traces from the 1 and 10 rad s$^{-1}$ experiments converge. Re-exposure of the sample at 180 s returns the gel to its previous viscoelastic storage modulus as it continues toward the final elastic modulus and the photoinitiator is completely consumed (photoinitiator half-life=45 s, Equation 1). Clearly, these reaction conditions result in rapid but incomplete photodegradation. Examination of the relevant functional groups—LAP (4×10$^{-3}$ m) and initial network thioethers (16.5×10$^{-3}$ m)—can help explain this. According to the Flory-Stockmayer equation [52], the gel point for this hydrogel is estimated as ≈61% (Equation 2), meaning that 39%, or 6.5×10$^{-3}$ m, of crosslinks would need to be cleaved to achieve reverse gelation. Theoretically, if every initiator fragment added directly to a crosslinking olefin, it would be possible to cause reverse gelation. However, proton abstraction from the increasing number of liberated pendant thiols may bias the system toward reactions that do not result in a net change in the crosslink density.

$$\frac{d[LAP]}{dt} = \frac{\varepsilon \ln(10) \phi I_0 \lambda}{N_{AV} hc} \qquad \text{Equation 1}$$

Equation 1 shows the Photoinitiator lifetime. For a thin film, the photoinitiator lifetime can be calculated as shown above, where molar absorptivity ε=218 M$^{-1}$ cm$^{-1}$, intensity of incident light $I_0$=10 mW/cm$^2$, wavelength λ=365 nm, quantum yield ϕ is assumed to be unity, Avogadro's number $N_{AV}$, Planck's constant h, and the speed of light c. Solving, the photoinitiator follows first order decay with a rate constant of 0.015 s$^{-1}$. This corresponds to a half-life of 45 s.

Equation 2 shows the Flory-Stockmayer percolation threshold for a step growth polymer network:

$$p_c = \frac{1}{\sqrt{r(f_a - 1)(f_b - 1)}} \qquad \text{Equation 2}$$

with functionalities of the PEG-DBCO ($f_a$=4) and the azide crosslinker ($f_b$=2) and a stoichiometric ratio r=0.91 gives the critical conversion for gelation as pc=0.61

Figure 3C:
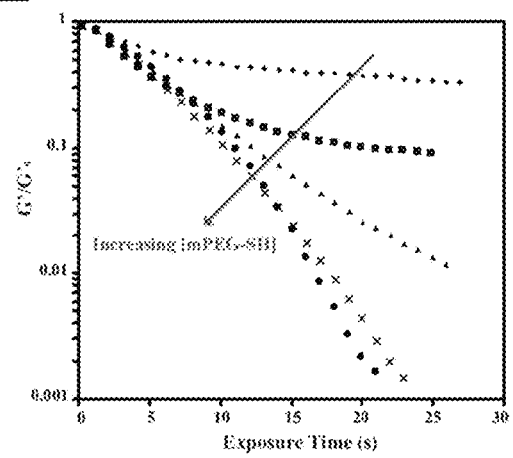

To increase the efficiency of the photodegradation reaction and allow complete network degradation, the AFCT reaction in the presence of a free monothiol (mPEG-SH) was studied. In contrast to network-bound thiols, addition by a monofunctional thiol changes the overall network connectivity and effectively cleaves crosslinks. These replacement reactions can be favored by increasing the concentration of free monothiol relative to the concentration of thioethers initially present in the network. mPEG-SH was introduced at concentrations ranging from 5×10$^{-3}$ to 50×10$^{-3}$ m, along with 4×10$^{-3}$ m LAP and irradiated with 365 nm light at 10 mW cm$^{-2}$. As seen in FIG. 3C, 25×10$^{-3}$ and 50×10$^{-3}$ m of mPEG-SH resulted in reverse gelation, while concentrations of 0×10-, 5×10$^{-3}$, or 15×10$^{-3}$ m did not. If one assumes similar reactivity of the alkyl thiols from mPEG-SH and the liberated network thiols, it may be expected that the various thiolated molecules in FIG. 1 would be expected to approach an equilibrium defined by Equation 3:

$$k_{eq} = \frac{[\text{free } mPEG\text{-}SH][\text{network thioether}]}{[\text{liberated network thiol}][\text{tethered } mPEG\text{-}Sh]} = \qquad \text{Equation 3}$$

$$\frac{([mPEG\text{-}SH]_0 - x)(16.5 \times 10^{-3} M - x)}{x^2} - 1$$

Figure 10:
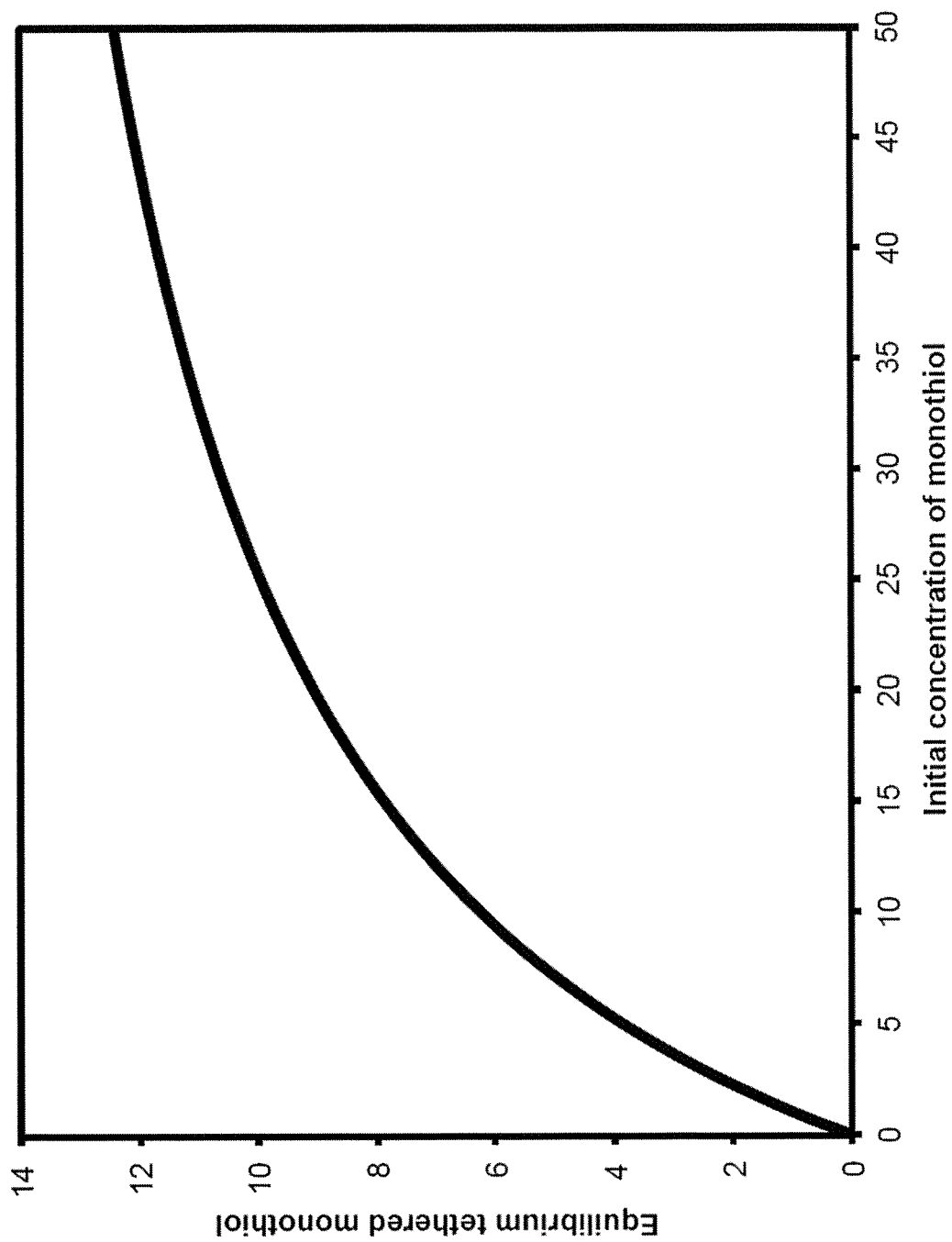
FIG. 10 shows the diminishing returns of increasing the concentration of free monothiol. The equilibrium amount of tethered monothiol approaches the initial thioether concentration (16.5 mM) at infinite [mPEG-SH]$_0$.
Figure 11:
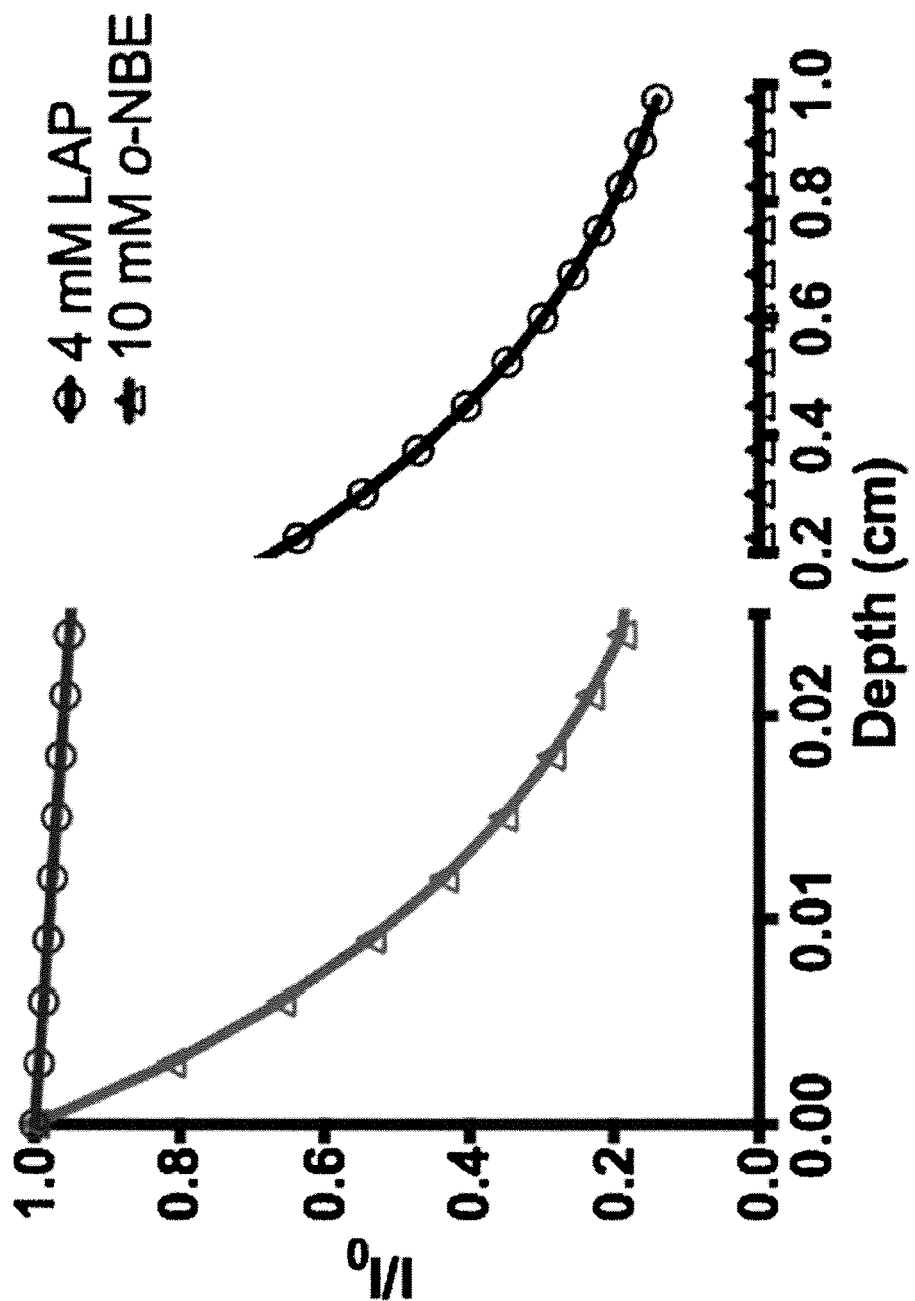
FIG. 11 shows theoretical light attenuation at 365 nm in a hydrogel containing 4 mM LAP ($\varepsilon$=218 M$^{-1}$ cm$^{-1}$) compared to one containing 10 mM nitrobenzyl ester linkages (assuming $\varepsilon$=3000 M$^{-1}$ cm$^{-1}$).

FIG. 10 shows the expected equilibrium as a function of initial monothiol concentration. The predicted amount of initial free monothiol needed to cleave 6.5×10$^{-3}$ m crosslinks is 11×10$^{-3}$ m, and thus, one may expect complete degradation at 15×10$^{-3}$ m. Instead, a very weak gel with G'≈1% of its initial value was found. It is possible that increasing the photoinitiator concentration would allow this equilibrium to be reached, but the competing reaction of initiator with olefin makes this analysis complex.

Figure 4A:
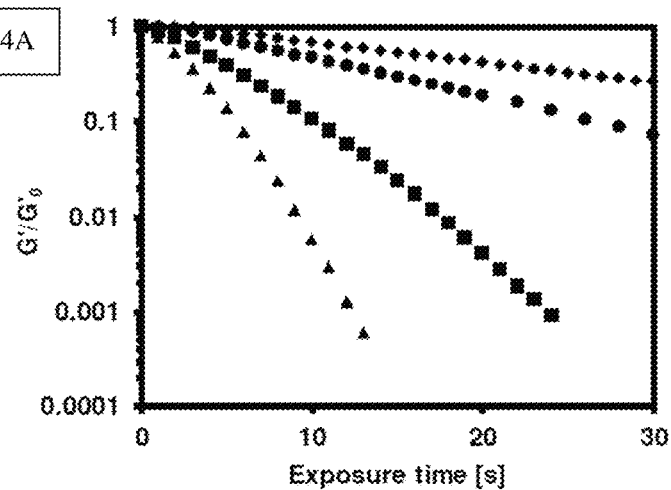
FIG. 4A-C shows photodegradation kinetics can be adjusted by changes in either the photoinitiator concentration or light intensity. Light intensity (l) as a function of depth (d) within a hydrogel containing an absorbing molecule with molar absorptivity ε and concentration c were calculated as in Equation 4.
Figure 4B:
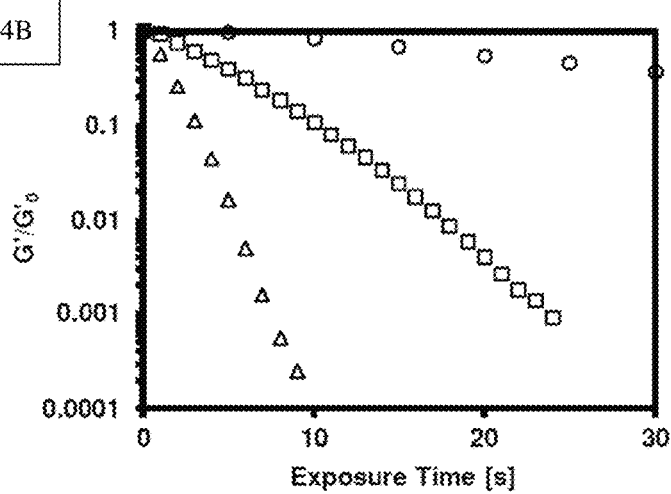
Figure 4C:
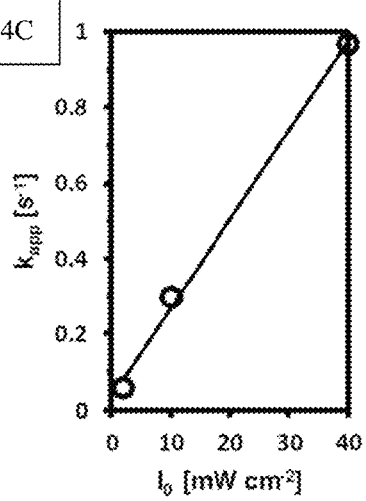

The effect of varying photoinitiator concentration was also investigated while keeping free thiol concentration constant at 25×10$^{-3}$ m and light intensity constant at 10 mW cm$^{-2}$ (FIG. 4A). Light intensity (l) as a function of depth (d) within a hydrogel containing an absorbing molecule with molar absorptivity ε and concentration c were calculated as in Equation 4. As expected, the photoinitiator concentration had a strong effect on both the rate and extent of photodegradation. By increasing the photoinitiator concentration to 8×10$^{-3}$ m, complete reverse gelation was achieved after <13 s of irradiation, corresponding to a rate constant of $k_{app}/I_0$×10$^{-4}$ of 580 cm$^2$ mW$^{-1}$ s$^{-1}$ and a photodegradation half-life of under 2 s. This result was compared to the rate of photodegradation of the widely used orthonitrobenzyl group and coumarin groups, and the AFCT mode of degradation was 70-2000 times faster than photodegradation methods based on alpha cleavage [10, 18, 21, 23, 53-55]. The effect of light intensity on the degradation rate was then studied (FIG. 4B). The rate of photodegradation was easily tuned by setting the intensity of the illuminating light to 2, 10, or 40 mW cm$^{-3}$. For $4\times10^{-3}$ m LAP and $25\times10^{-3}$ m mPEG-SH, a plot of $k_{app}$ versus I0 yields a straight line with a slope of $235\times10^{-4}$ cm$^2$ mW$^{-1}$ s$^{-1}$ (FIG. 4C).

$$\frac{I}{I_0} = e^{-ln(10)\varepsilon cd} \quad \text{Equation 4}$$

AFCT-based photodegradable hydrogels also benefit from decreased light attenuation. There are two underlying causes to this effect. First, the molar absorptivity of one chosen photoinitiator, LAP, at 365 nm is 218 m$^{-1}$ cm$^{-1}$ [41]. This is in contrast to the ortho-nitrobenzyl ester and coumarin photolabile groups which have molar absorptivities on the order of 3000 to 7000 m$^{-1}$ cm$^{-1}$ at 365 nm [18, 23, 54], and while more transparent at longer wavelengths, the quantum yield and efficiency also decrease. The other contributing factor is that the concentration of photoactive species in this case can be lower because the radicals generated can propagate through numerous photocleavage events. In practice, $4\times10^{-3}$ m LAP was found to be sufficient for complete photodegradation, in comparison to $10\times10^{-3}$ and $40\times10^{-3}$ m nitrobenzyl photodegradable groups commonly employed in photodegradable polymer strands. The combination of these factors allowed for photodegradation of much thicker hydrogel samples. To demonstrate the power of this effect, a 1 cm thick hydrogel with $4\times10^{-3}$ m LAP was created and subsequently swelled in mPEG-SH to a final concentration of $25\times10^{-3}$ m. The swollen hydrogen was then exposed to 365 nm light at 10 mW cm$^{-2}$ along the 1 cm axis. For the LAP concentration employed, this 1 cm sample still allows ≈13% transmission of the incident light at the bottom of the sample (Equation 5). As observed macroscopically in FIG. 5A, this hydrogel rapidly erodes in ≈1 min. which renders this hydrogel chemistry particularly useful for certain biomaterials applications. For example, in applications where one may wish to harvest selected cells or the entire cell population (e.g., for fluorescence-activated cell sorting or other analyses), light exposure in defined regions can allow cell capture in a manner akin to laser capture microdissection. In addition, as the field of mechanotransduction transitions from 2D to 3D culture systems, there is an ever increasing need for ways to expand and passage cells in 3D environments. One major roadblock in this approach is how to harvest cells from these 3D materials for further expansion or characterization. Photodegradation is one attractive option, due to the spatial and temporal control that can be leveraged to release defined regions of cells at user-specified time points. However, rapid and spatially defined erosion is required, and current systems can be limited by relatively slow degradation kinetics and significant light attenuation. The aforementioned qualities of allyl sulfide crosslinked hydrogels give potential utility in this regard.

Equation 5 shows the equilibrium approached by thiolated molecules of FIG. 9.

$$K_{eq} = \frac{[\text{free } mPEG\text{-}SH][\text{network thioether}]}{[\text{liberated network thiol}][\text{cleaved } xlinks]} = \frac{([mPEG\text{-}SH]_0 - x)(16.5 - x)}{x^2} \quad \text{Equation 5}$$

where x=tethered mPEG-SH=liberated network thiol=cleaved crosslinks

Figure 7:
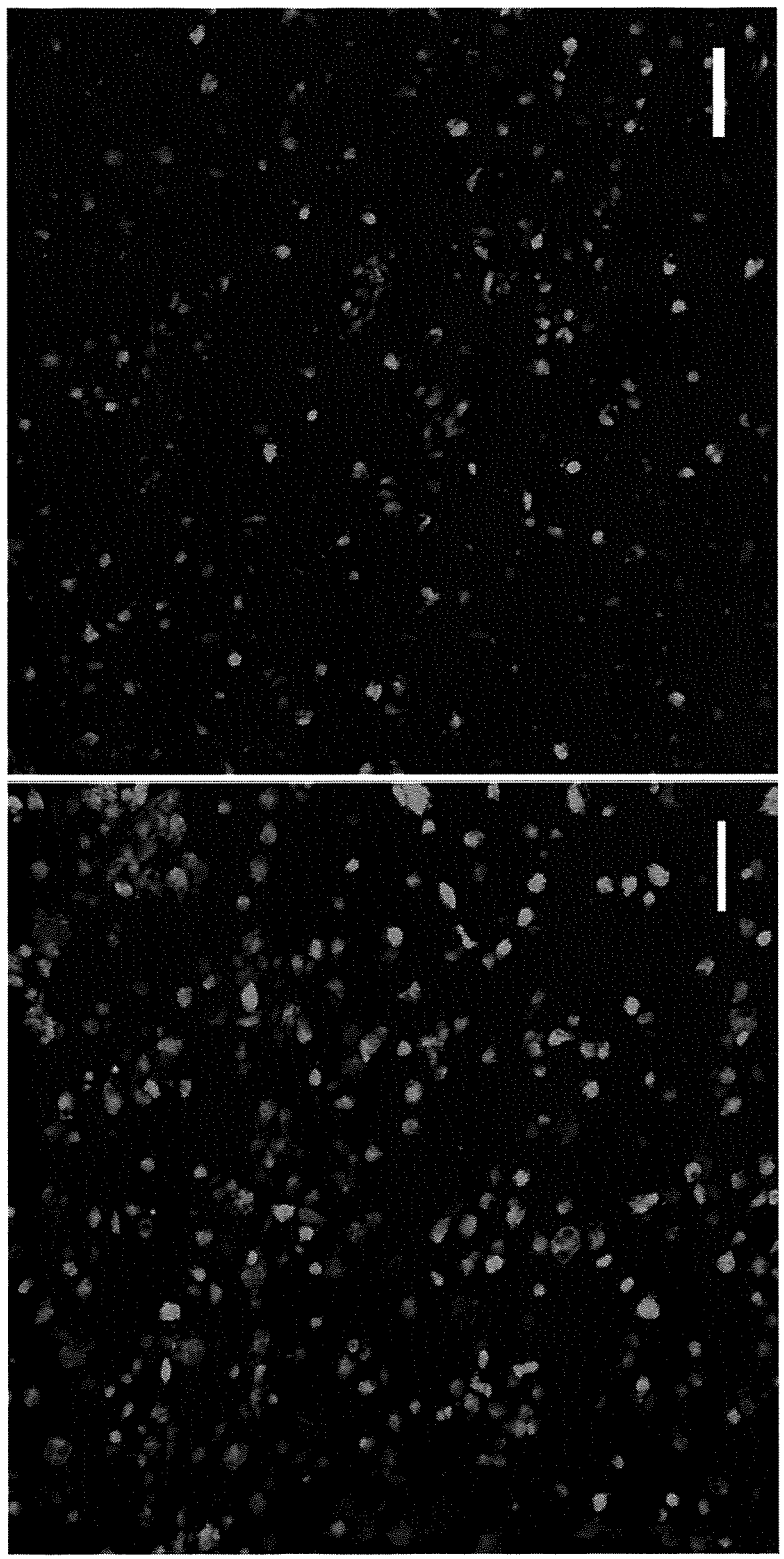
FIG. 7 shows encapsulated hMSC cell viability. Representative projections of 3D confocal images acquired at day 1 (left, 90% viable) and day 4 (right, 70% viable). Cells are stained with calcein AM (live—green) and ethidium homodimer (red—dead). Scale bar 100 µm.

To demonstrate some of these advantages, primary human mesenchymal stem cells (hMSCs) were encapsulated in 3 mm thick hydrogels at a density of $5\times10^6$ cells mL$^{-1}$. For all of the cell culture experiments, an azide-functionalized RGD peptide was added to the gel formulation at $1\times10^{-3}$ m to provide cell-matrix interactions. Encapsulation using the SPAAC reaction is known to proceed with high cell viability [18]; indeed, hMSC viability was quantified as 90% and 74% after 1 and 4 d of encapsulation, respectively (FIG. 7). This reduction in cell viability over time may be attributed, in part, to the inability of these encapsulated cells to remodel the PEG networks [56], but the chemistry is readily modified to include protease degradable peptide linkers.

Figure 5C:
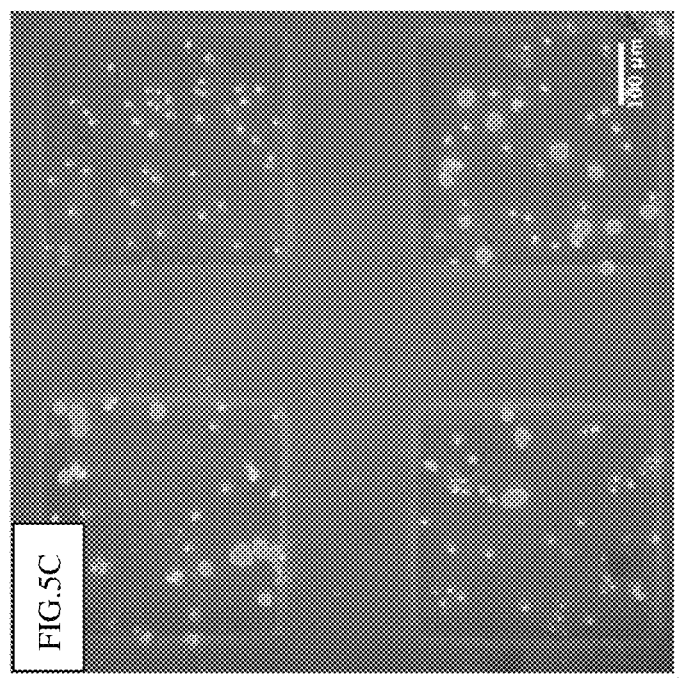
FIG. 5A-C shows allyl sulfide-based photodegradable hydrogels can be used for large scale erosion and cytocompatible cell release.
Figure 5B:
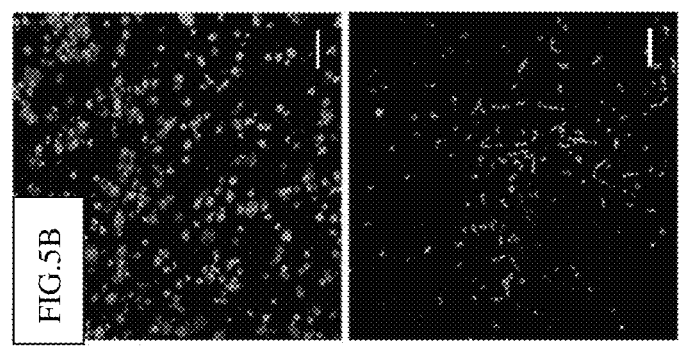
Figure 5A:
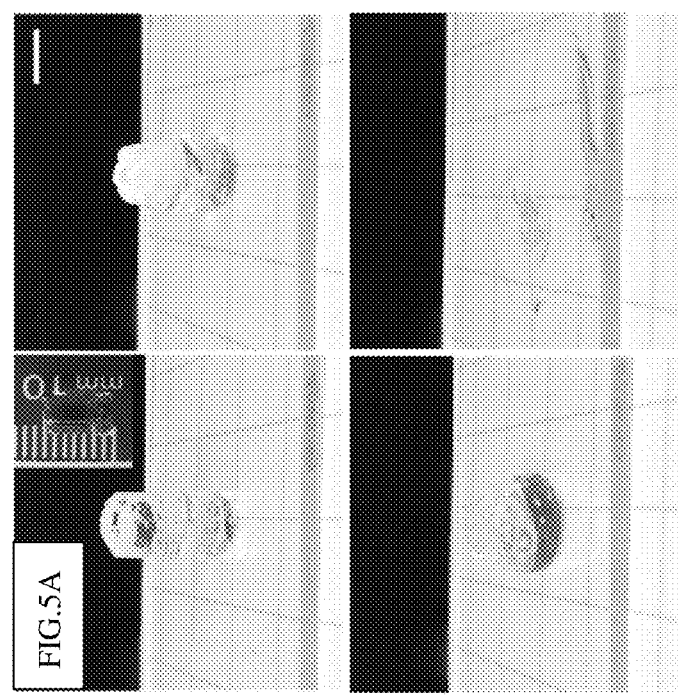
Figure 8:
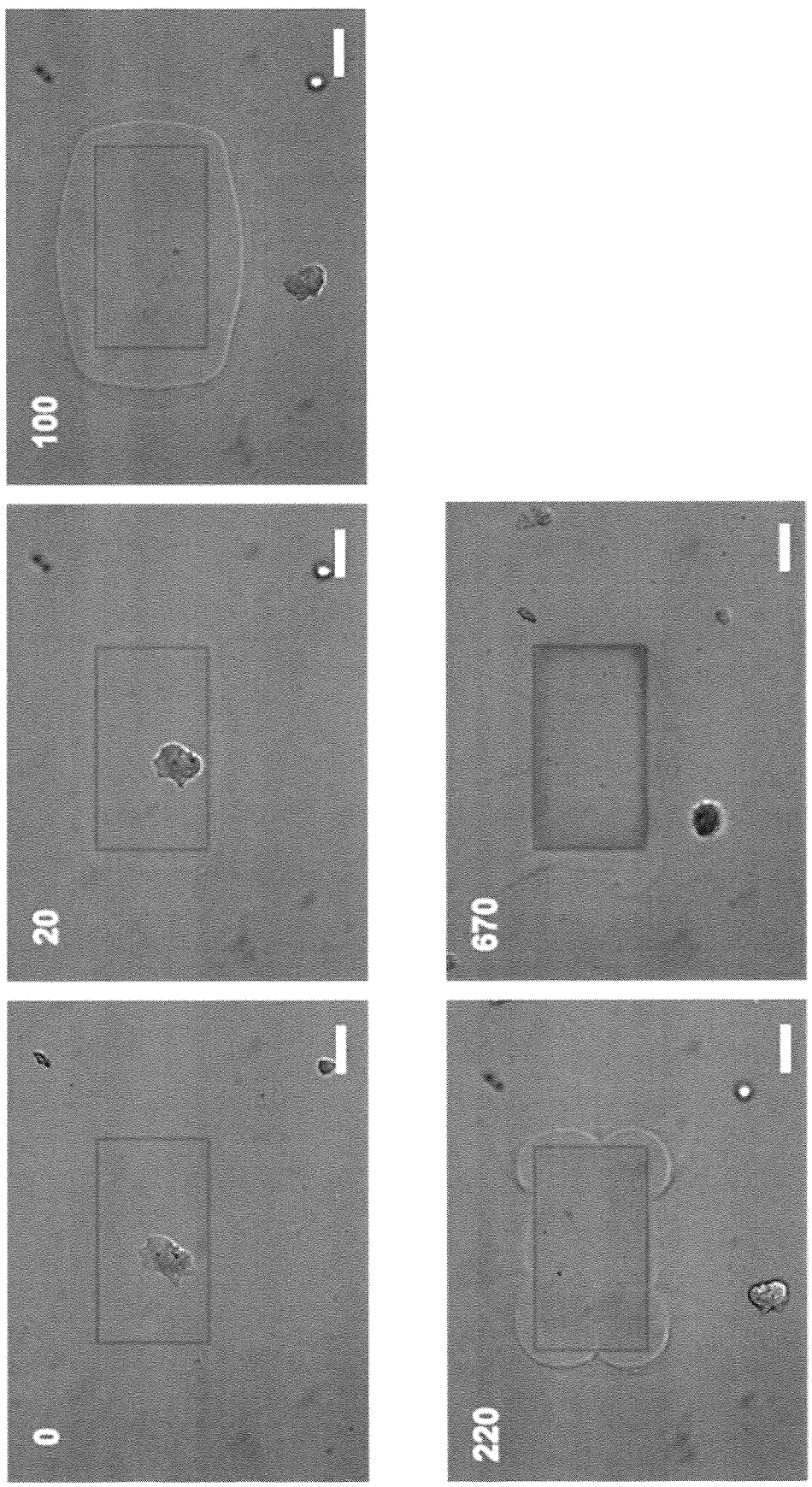
FIG. 8 shows the photodegradation and release of a cell on confocal microscope. A user defined area (red box) containing an adhered hMSC was repeatedly scanned with a 405 nm laser on a confocal laser scanning microscope, causing release of the adhered cell by 100 scans and complete gel degradation by 670 scans. Upper right=number of scans with 405 nm light. Scale bar=50 µm.

After 1 d of encapsulation, the cell laden hydrogels were swollen with mPEG-SH ($50\times10^{-3}$ m) and LAP ($4\times10^{-3}$ m) for 1 h, followed by exposure to 10 mW cm$^{-2}$ of 365 nm light for 1 min on a gelatin coated glass coverslip (FIG. 5B). Under these exposure conditions, $2.4\times10^{-3}$ m photoinitiator is consumed, which is similar to photoinitiator concentrations that have been widely found to be cytocompatible for photoencapsulation and photopatterning [5, 41, 57-59]. The encapsulated cells were released from the photodegradable hydrogel and allowed to adhere to the underlying glass coverslip under standard culture conditions. hMSCs were viable upon release, and spread on the coverslip over 24 h, which demonstrates that these reaction conditions are mild enough to be useful for 3D cell culture and capture. Spatial control over cell release was also achieved under the same conditions by selective exposure of a 150 μm thick hydrogel through a chrome photomask (FIG. 5C). In addition, the absorption spectrum of LAP was taken advantage of, which extends up to 450 nm, to demonstrate that these hydrogels are capable of photodegradation under 405 nm light for cell release using a conventional microscope setup. hMSCs were seeded onto hydrogels at $1\times10^4$ cells cm$^{-2}$ and using a confocal laser scanning microscope with a 405 nm laser (DAPI channel) at 60% power, a user defined area of the gel was degraded to release an adhered cell (FIG. 8).

In conclusion, a photodegradable hydrogel system was synthesized incorporating an allyl sulfide functionality that allowed for a radical-initiated thiol-ene exchange reaction. By the introduction of monothiols, the network connectivity and mechanical properties could be controlled on-demand by exposure to light. Under conditions that proved cytocompatible ($4\times10^{-3}$ m LAP, $25\times10^{-3}$ m mPEG-SH, 10 mW cm$^{-2}$ 365 nm light), reverse gelation occurred in under 30 s and samples up to 1 cm thick could be eroded in ≈1 min, representing a significant benefit over conventional photodegradable hydrogels in both respects.

Importantly, both the SPAAC gel formation and photodegradation processes were designed to be compatible with biological systems, allowing new-found experiments to study cells in dynamic environments, and to readily capture cells from 3D laden systems. This new class of photodegradable hydrogels is unique in its mechanism, speed of degradation, and depths attainable, and provides access to experiments previously limited by light dose and attenuation.

EXAMPLES

The following examples are provided in order to demonstrate and further illustrate certain preferred embodiments and aspects of the present invention and are not to be construed as limiting the scope thereof. $^1$H-NMR spectra were performed on a 400 MHz Bruker NMR spectrometer, where the residual proton resonance of the solvent is used as an internal standard for each molecule. Chemical shifts are shown in parts per million (ppm). The multiplicities of each peak are given in abbreviations such as: s, singlet; d, doublet; t, triplet; m, multiplet; q, quartet. All chemicals used were purchased from commercial sources and used as such, unless otherwise mentioned.

Example 1

Synthesis of Compound 1 [Allyl Sulfide Bis(Methyl Ester)]

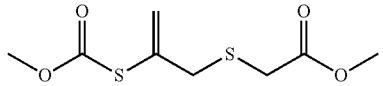

Sodium (1.1 g, 48 mmol) was added to a flame dried flask charged with 150 mL anhydrous methanol and allowed to react for 10 minutes. After dissolution of the sodium, methyl thioglycolate (3.93 mL, 44 mmol) was added to the flask and the mixture was heated to reflux under an argon atmosphere and reacted for 20 minutes. 3-chloro-2-chloromethyl-1-propene (2.31 mL, 20 mmol) dissolved in 20 mL anhydrous methanol was then added dropwise to the reaction vessel over 45 minutes. The reaction mixture was purged with argon and stirred for 18 h at 60° C. The resulting mixture was filtered and concentrated through rotary evaporation to yield a yellow crude oil. The crude oil was taken up in 100 mL MQ water and extracted 6× with 100 mL diethyl ether (Et$_2$O). The combined organic phases were washed with 200 mL brine, dried over sodium sulfate and concentrated by rotary evaporation to yield a pale yellow oil (2.88 g, 55%).

TLC in 80% hexanes:20% ethyl acetate reveals a single spot at R$_f$=0.27 under UV, I$_2$, and PMA. $_1$H NMR (400 MHz, Methanol-d$_4$) δ 5.11 (q, J=0.6 Hz, 2H), 3.72 (s, 6H), 3.42 (t, J=0.7 Hz, 4H), 3.21 (s, 4H).

Example 2

Synthesis of Compound 2 [Allyl Sulfide Bis(Acetic Acid)]

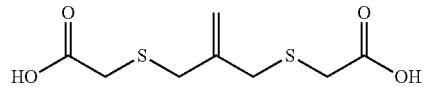

100 ml of 1M LiOH (aq) was added to a solution of 1 (2.88 g, 10.9 mmol) in 100 ml THF on ice. The turbid solution was stirred for 5 h on ice, after which the solution was acidified (to pH=0) by addition of ~100 mL 2M HCl. 50 ml brine was added and the solution was extracted with EtOAc (4×125 ml). The combined organics were dried over Na$_2$SO$_4$ and concentrated to yield a dark brown oil (2.57 g, 100%)

$^1$H NMR (400 MHz, DMSO-d$_6$) δ 12.58 (s, 2H), 5.04 (s, 2H), 3.32 (d, J=0.8 Hz, 4H), 3.14 (s, 4H).

Example 3

Synthesis of Compound 3 [Allyl Sulfide Bis(PEG3-Azide)]

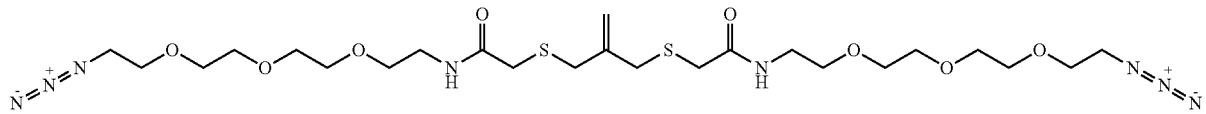

A flame dried RBF was charged with 2 (360 mg, 1.53 mmol), diisopropylethylamine (DIEA, Sigma) (2.7 mL, 15.3 mmol), O-(7-Azabenzotriazol-1-yl)-N,N,N',N'-tetramethyluronium hexafluorophosphate (HATU, Chem-Impex Int'l) (1.16 g, 3.05 mmol), and 250 mL ethyl acetate. The resulting slurry was purged with argon and reacted for 1 hr at room temperature. 11-Azido-3,6,9-trioxaundecan-1-amine (TCI America) (1 g, 4.58 mmol) was added to the flask and the mixture was stirred overnight at room temperature under an argon atmosphere. The resulting mixture was vacuum filtered and washed with 1N HCl (1×250 mL), saturated aq. sodium bicarbonate (1×250 mL), water (1×100 mL), and brine (1×100 mL). The organic phase was dried over sodium sulfate and concentrated to yield a dark yellow oil (646 mg, 66%). TLC in 80% acetone:20% hexanes revealed a single spot at R$_f$=0.3 with b staining.

₁H NMR (400 MHz, Methanol-d₄) δ 5.12 (s, 2H), 4.66 (s, 2H), 3.73-3.62 (m, 20H), 3.58 (t, J=5.4 Hz, 4H), 3.43-3.36 (m, 12H), 3.16 (s, 4H).

ESI+ HRMS: calc'd for $[C_{24}H_{44}N_8O_8S_2+H]+$: 637.2797, found 637.2805.

Example 4

Synthesis of PEG-DBCO

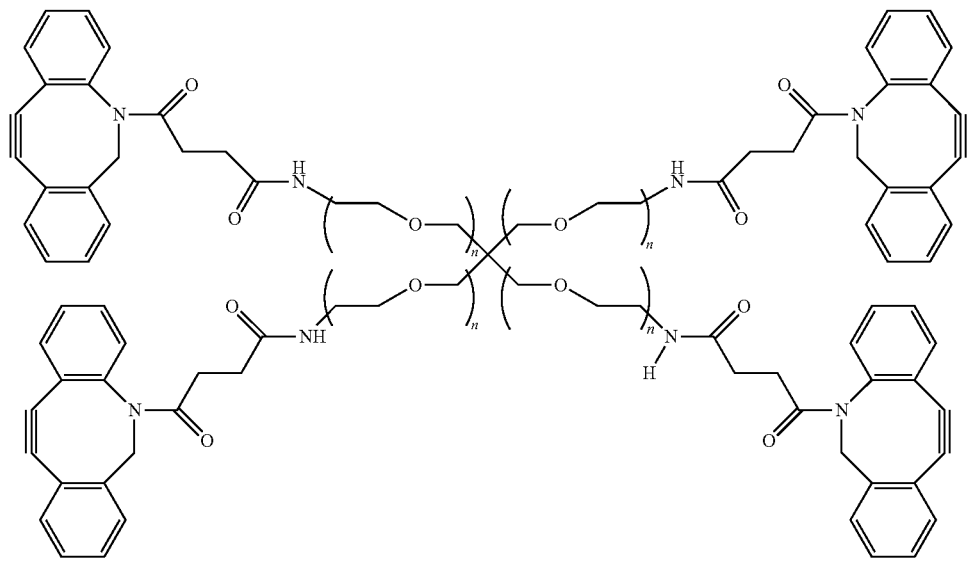

A solution of HATU (125 mg, 0.33 mmol). DIEA (78 mg, 0.6 mmol), and dibenzocyclooctyne acid (Click Chemistry Tools) (100 mg, 0.3 mmol) in DMF was stirred for 10 minutes, followed by addition of 4 arm PEG amine (MW=20 kDa, Jenkem Technology USA) (750 mg, 0.037 mmol). The solution was Argon purged and allowed to react for 24 h at room temperature. The product was precipitated in cold Et₂O (200 ml), and washed with cold Et₂O (2×200 ml). The precipitate was dissolved in deionized water, dialyzed (MW cutoff 8 kDa) for 48 h, and lyophilized to yield 762 mg (95% yield). PEG functionalization was confirmed with $^1$H NMR to be ca. 95% by comparing characteristic peaks from DBCO to the PEG backbone peaks.

Example 5

Synthesis of RGD-Azide

The peptide GRGDS was synthesized via standard Fmoc solid phase peptide synthesis (Protein Technologies Tribute peptide synthesizer) and HATU activation using Rink amide resin. 4-azidobutanoic acid (prepared as previously described) [18] was coupled to the free N-terminus on resin via HATU coupling. The peptide was subsequently cleaved from the resin by treatment with 88:5:5:2 (trifluoroacetic acid:phenol:water:triisoproylsilane) for 2 hours and precipitated in cold Et₂O. Crude peptide was purified as needed by reverse phase HPLC (Waters Delta Prep 4000). MALDI-TOF: calc'd [M+H]+ 601.28, found 601.98 g/mol.

Example 6

Characterization of SPAAC Hydrogel Formation

Oscillatory rheology was performed on a TA Instruments DHR-3 rheometer with an 8 mm parallel plate geometry and a quartz lower plate to allow UV illumination. Allyl sulfide crosslinked SPAAC hydrogels were prepared by mixing stock solutions of 20 wt % PEG-DBCO in phosphate buffered saline (PBS) and 30 mM allyl sulfide bis(azide) 2 in 1:1 DMSO:distilled H₂O to a final concentration of 7.5 wt % PEG-DBCO and 8.25 mM 2 in PBS. The precursor solution was vortexed for 5 s and placed on the rheometer with the gap immediately lowered to 260 μm. Hydrogel gelation kinetics were characterized and evaluated in situ by

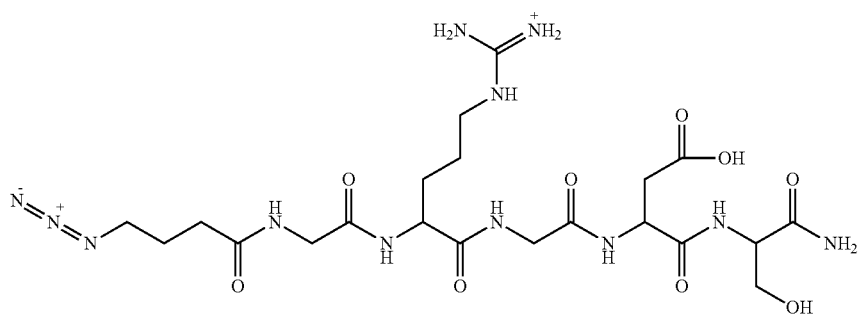

measuring the evolution of the storage and loss moduli (G' and G"). Measurements were taken with an oscillatory shear strain of 1% and a frequency of 1 rad/s (within the linear viscoelastic range).

Example 7

Characterization of Hydrogel Photodegradation

This rheometer was fitted with an adaptor to allow for light exposure from a mercury arc lamp (Omnicure) fitted with a 365 nm bandpass filter in order to monitor gel degradation during exposure to UV light. Allyl sulfide crosslinked hydrogels were synthesized as described in the previous section and were allowed to gel completely (as determined by a negligible change in G' with respect to time; about 10 minutes). After this point, the tool was carefully lifted and the gel immersed in a bath to bring the final concentration to the desired level of photoinitiator and monothiol. After 20 min, a swell time which was determined to be sufficient to attain a near uniform concentration profile throughout the sample (see next section), the gel was exposed to 365 nm light at an intensity of 2, 10, or 40 mW cm$^{-2}$. Measurements were taken with an oscillatory shear strain of 1% and a frequency of 1 rad/s. Due to the rapid reorganization of the network, it was necessary to shutter the light after consecutive 1 s exposures to obtain accurate G' readings. The measurement was allowed to stabilize in the dark between each 1 s exposure, and the storage modulus was recorded.

Example 8

Calculation of Swelling Time

Figures 6A, 6B:
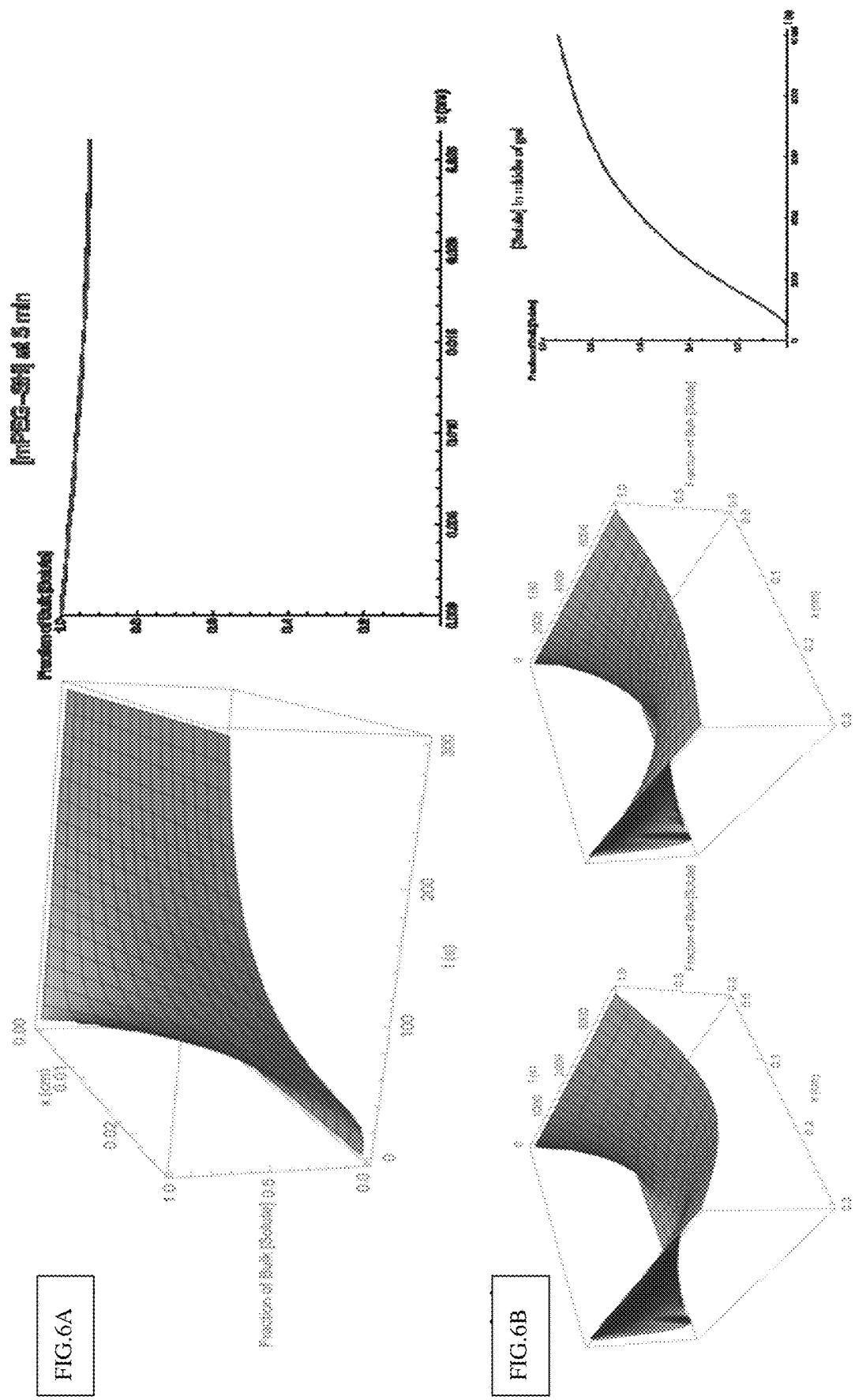
FIGS. 6A&B show modeling diffusion of mPEG-SH within a hydrogel.
FIG. 6B shows the concentration profile of mPEG-SH within a 3 mm thick hydrogel over a 1 h (left panel) and 2 h (middle panel) swell time when immersed in a mPEG-SH bath. The right panel shows that the mPEG-SH concentration in the middle of the 3 mm thick hydrogel is about 40% that of the bulk at 1 h. At a bulk mPEG-SH concentration of 50 mM the minimum concentration in the hydrogel at 1 hr is about 20 mM mPEG-SH, a concentration that was shown to be sufficient for photodegradation.

A diffusion model using Ficks Laws was set up in Mathematica to determine the minimum amount of time required to achieve a nearly uniform concentration profile of the photodegradation components throughout the hydrogel samples in the experiments. Do was assumed equal to that of PEG$_{600}$ (2.6×10$^{-6}$ cm$^2$ s$^{-1}$) [60] in all simulations. For the rheological experiments modeled in FIG. 6A, a no-flux boundary condition was used at the bottom of the hydrogel and the bulk mPEG-SH concentration was used as the boundary condition at the top of the hydrogel; it was assumed that there was no mPEG-SH within the hydrogel initially. For the cell-laden hydrogel photodegradation experiments modeled in FIG. 6b, it was assumed that there was no mPEG-SH in the gel initially and the concentration at the top and bottom of the hydrogel were that of the bulk solution for all time.

Thus, specific compositions and methods of amplified photodegradation of hydrogels and methods of producing the same have been disclosed. It should be apparent, however, to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

REFERENCES

1. Parhi, R. (2017) "Cross-Linked Hydrogel for Pharmaceutical Applications: A Review," *Adv. Pharm. Bull.* 7(4), 515-530.
2. Jenkins, A. D. et al. (2009) "Terminology for Reversible-Deactivation Radical Polymerization Previously Called "Controlled" Radical or "Living" Radical Polymerization (Iupac Recommendations 2010)," *Pure Appl. Chem.* 82(2), 483-491.
3. Hoffman, A. S. (2012) "Hydrogels for Biomedical Applications," *Adv. Drug Delivery Rev.* 64, Supplement, 18-23.
4. Annabi, N. et al. (2014) "25th Anniversary Article: Rational Design and Applications of Hydrogels in Regenerative Medicine," *Adv. Mater.* 26(1), 85-124.
5. Han, L.-H. et al. (2014) "Photo-Crosslinkable PEG-Based Microribbons for Forming 3D Macroporous Scaffolds with Decoupled Niche Properties," *Adv. Mater.* 26(11), 1757-1762.
6. McCall, J. D. and Anseth, K. S. (2012) "Thiol-Ene Photopolymerizations Provide a Facile Method to Encapsulate Proteins and Maintain Their Bioactivity," *Biomacromolecules* 13(8), 2410-2417.
7. Burdick, J. A. and Anseth, K. S. (2002) "Photoencapsulation of Osteoblasts in Injectable RGD-Modified PEG Hydrogels for Bone Tissue Engineering," *Biomaterials* 23(22), 4315-4323.
8. Khetan, S. and Burdick, J. A. (2010) "Patterning Network Structure to Spatially Control Cellular Remodeling and Stem Cell Fate within 3-Dimensional Hydrogels," *Biomaterials* 31(32), 8228-8234.
9. DeForest, C. A. and Tirrell, D. A. (2015) "A Photoreversible Protein-Patterning Approach for Guiding Stem Cell Fate in Three-Dimensional Gels," *Nat. Mater.* 14(5), 523-531.
10. Kloxin, A. M. et al. (2009) "Photodegradable Hydrogels for Dynamic Tuning of Physical and Chemical Properties," *Science* 324(5923), 59-63.
11. Khetan, S. et al. (2013) "Degradation-Mediated Cellular Traction Directs Stem Cell Fate in Covalently Crosslinked Three-Dimensional Hydrogels," *Nat. Mater.* 12(5), 458-465.
12. Gandavarapu, N. R. et al. (2014) "Photo-Click Living Strategy for Controlled, Reversible Exchange of Biochemical Ligands," *Adv. Mater.* 26(16), 2521-2526.
13. Mosiewicz, K. A. et al. (2013) "In Situ Cell Manipulation through Enzymatic Hydrogel Photopatterning," *Nat. Mater.* 12(11), 1072-1078.
14. Highley, C. B. et al. (2015) "Direct 3D Printing of Shear-Thinning Hydrogels into Self-Healing Hydrogels," *Adv. Mater.* 27(34), 5075-5079.
15. Hinton, T. J. et al. (2015) "Three-Dimensional Printing of Complex Biological Structures by Freeform Reversible Embedding of Suspended Hydrogels," *Science Advances* 1(9).
16. Metters, A. T. et al. (2001) "A Statistical Kinetic Model for the Bulk Degradation of Pla-B-PEG-B-Pla Hydrogel Networks: Incorporating Network Non-Idealities," *J. Phys. Chem. B* 105, 8069-8076.
17. Lutolf, M. P. et al. (2003) "Synthetic Matrix Metalloproteinase-Sensitive Hydrogels for the Conduction of Tissue Regeneration: Engineering Cell-Invasion Characteristics," *P.N.A.S.* 100(9), 5413-5418.
18. DeForest, C. A. and Anseth, K. S. (2011) "Cytocompatible Click-Based Hydrogels with Dynamically-Tunable Properties through Orthogonal Photoconjugation and Photocleavage Reactions," *Nature Chemistry* 3(12), 925-931.
19. Kloxin, A. M. et al. (2010) "In Situ Elasticity Modulation with Dynamic Substrates to Direct Cell Phenotype," *Biomaterials* 31(1), 1-8.
20. Yang, C. et al. (2014) "Mechanical Memory and Dosing Influence Stem Cell Fate," *Nat. Mater.* 13(6), 645-652.
21. Azagarsamy, M. A. et al. (2014) "Coumarin-Based Photodegradable Hydrogel: Design, Synthesis, Gelation, and Degradation Kinetics," *ACS Macro Letters* 3(6), 515-519.
22. McKinnon, D. D. et al. (2014) "Design and Characterization of a Synthetically Accessible, Photodegradable Hydrogel for User-Directed Formation of Neural Networks," *Biomacromolecules* 15(7), 2808-2816.
23. Griffin, D. R. and Kasko, A. M. (2012) "Photodegradable Macromers and Hydrogels for Live Cell Encapsulation and Release," *J. Am. Chem. Soc.* 134(31), 13103-13107.
24. Norris, S. C. P. et al. (2016) "Direct Gradient Photolithography of Photodegradable Hydrogels with Patterned Stiffness Control with Submicrometer Resolution," *ACS Biomaterials Science & Engineering* 2(8), 1309-1318.
25. Tsang, K. M. C. et al. (2015) "Facile One-Step Micropatterning Using Photodegradable Gelatin Hydrogels for Improved Cardiomyocyte Organization and Alignment," *Adv. Funct. Mater.* 25(6), 977-986.
26. Scott, T. F. et al. (2005) "Photoinduced Plasticity in Cross-Linked Polymers," *Science* 308(5728), 1615.
27. Scott, T. F. et al. (2006) "Actuation in Crosslinked Polymers Via Photoinduced Stress Relaxation," *Adv. Mater.* 18(16), 2128-2132.
28. Kloxin, C. J. et al. (2009) "Stress Relaxation Via Addition—Fragmentation Chain Transfer in a Thiol-Ene Photopolymerization," *Macromolecules* 42(7), 2551-2556.
29. Evans, R. A. and Rizzardo, E. (2000) "Free-Radical Ring-Opening Polymerization of Cyclic Allylic Sulfides. 2. Effect of Substituents on Seven- and Eight-Membered Ring Low Shrink Monomers," *Macromolecules* 33(18), 6722-6731.
30. Tibbitt, M. W. et al. (2013) "Modeling Controlled Photodegradation in Optically Thick Hydrogels," *J. Polym. Sci. A Polym. Chem.* 51(9), 1899-1911.
31. Jewett, J. C. et al. (2010) "Rapid Cu-Free Click Chemistry with Readily Synthesized Biarylazacyclooctynones," *J. Am. Chem. Soc.* 132(11), 3688-3690.
32. DeForest, C. A. et al. (2009) "Sequential Click Reactions for Synthesizing and Patterning 3D Cell Microenvironments," *Nat. Mater.* 8(8), 659-664.
33. Ekkebus, R. et al. (2013) "On Terminal Alkynes That Can React with Active-Site Cysteine Nucleophiles in Proteases," *J. Am. Chem. Soc.* 135(8), 2867-2870.
34. Shiu, H.-Y. et al. (2009) "Electron-Deficient Alkynes as Cleavable Reagents for the Modification of Cysteine-Containing Peptides in Aqueous Medium," *Chemistry—A European Journal* 15(15), 3839-3850.
35. Shiu, H.-Y. et al. (2010) "A Highly Selective FRET-Based Fluorescent Probe for Detection of Cysteine and Homocysteine," *Chemistry—A European Journal* 16(11), 3308-3313.
36. van Geel, R. et al. (2012) "Preventing Thiol-Yne Addition Improves the Specificity of Strain-Promoted Azide-Alkyne Cycloaddition," *Bioconjug. Chem.* 23(3), 392-398.
37. Chang, P. V. et al. (2010) "Copper-Free Click Chemistry in Living Animals," *P.N.A.S.* 107(5), 1821-1826.
38. Fairbanks, B. D. et al. (2010) "Reaction Rates and Mechanisms for Radical, Photoinitiated Addition of Thiols to Alkynes, and Implications for Thiol-Yne Photopolymerizations and Click Reactions," *Macromolecules* 43(9), 4113-4119.
39. Fairbanks, B. D. et al. (2009) "Thiol-Yne Photopolymerizations: Novel Mechanism, Kinetics, and Step-Growth Formation of Highly Cross-Linked Networks," *Macromolecules* 42(1), 211-217.
40. Majima, T. et al. (1991) "Phenyl-2,4,6-Trimethylbenzoylphosphinates as Water-Soluble Photoinitiators. Generation and Reactivity of O=$\dot{P}$(C6h5)(O—) Radical Anions," *Die Makromolekulare Chemie* 192(10), 2307-2315.
41. Fairbanks, B. D. et al. (2009) "Photoinitiated Polymerization of PEG-Diacrylate with Lithium Phenyl-2,4,6-Trimethylbenzoylphosphinate: Polymerization Rate and Cytocompatibility," *Biomaterials* 30(35), 6702-6707.
42. Moad, G. et al. (2008) "Radical Addition-Fragmentation Chemistry in Polymer Synthesis," *Polymer* 49(5), 1079-1131.
43. McKinnon, D. D. et al. (2014) "Biophysically Defined and Cytocompatible Covalently Adaptable Networks as Viscoelastic 3D Cell Culture Systems," *Adv. Mater.* 26(6), 865-872.
44. McKinnon, D. D. et al. (2014) "Bis-Aliphatic Hydrazone-Linked Hydrogels Form Most Rapidly at Physiological pH: Identifying the Origin of Hydrogel Properties with Small Molecule Kinetic Studies," *Chem. Mater.* 26(7), 2382-2387.
45. Rodell, C. B. et al. (2013) "Rational Design of Network Properties in Guest-Host Assembled and Shear-Thinning Hyaluronic Acid Hydrogels," *Biomacromolecules* 14(11), 4125-4134.
46. Lee, K. Y. and Mooney, D. J. (2012) "Alginate: Properties and Biomedical Applications," *Prog. Polym. Sci.* 37(1), 106-126.
47. Stowers, R. S. et al. (2015) "Dynamic Phototuning of 3D Hydrogel Stiffness," *Proc. Natl. Acad. Sci. U.S.A.* 112(7), 1953-1958.
48. Choudhury, S. et al. (2015) "A Highly Reversible Room-Temperature Lithium Metal Battery Based on Crosslinked Hairy Nanoparticles," *Nat. Commun.* 6, 10101.
49. Kloxin, C. J. and Bowman, C. N. (2013) "Covalent Adaptable Networks: Smart, Reconfigurable and Responsive Network Systems," *Chem. Soc. Rev.* 42(17), 7161-7173.
50. Rosales, A. M. and Anseth, K. S. (2016) "The Design of Reversible Hydrogels to Capture Extracellular Matrix Dynamics," *Nature Reviews Materials* 1, 15012.
51. Wang, H. and Heilshorn, S. C. (2015) "Adaptable Hydrogel Networks with Reversible Linkages for Tissue Engineering," *Adv. Mater.* 27(25), 3717-3736.
52. Stockmayer, W. H. (1943) "Theory of Molecular Size Distribution and Gel Formation in Branched-Chain Polymers," *J. Chem. Phys.* 11-55, 45.
53. Kloxin, A. M. et al. (2010) "Mechanical Properties of Cellularly Responsive Hydrogels and Their Experimental Determination," *Adv. Mater.* 22(31), 3484-3494.

54. Griffin, D. R. and Kasko, A. M. (2012) "Photoselective Delivery of Model Therapeutics from Hydrogels," *ACS Macro Letters* 1(11), 1330-1334.

55. DeForest, C. A. and Anseth, K. S. (2012) "Photoreversible Patterning of Biomolecules within Click-Based Hydrogels," *Angew Chem. Int. Ed.* 51(8), 1816-1819.

56. Hudalla, G. A. et al. (2008) "An Approach to Modulate Degradation and Mesenchymal Stem Cell Behavior in Poly(Ethylene Glycol) Networks," *Biomacromolecules* 9(3), 842-849.

57. Nichol, J. W. et al. (2010) "Cell-Laden Microengineered Gelatin Methacrylate Hydrogels," *Biomaterials* 31(21), 5536-5544.

58. Caliari, S. R. et al. (2016) "Stiffening Hydrogels for Investigating the Dynamics of Hepatic Stellate Cell Mechanotransduction During Myofibroblast Activation," *Sci. Rep.* 6, 21387.

59. Wong, D. Y. et al. (2015) "Low-Dose, Long-Wave Uv Light Does Not Affect Gene Expression of Human Mesenchymal Stem Cells," *PLoS. ONE* 10, 1.

60. Masaro, L. et al. (1999) "Self-Diffusion Studies of Water and Poly(Ethylene Glycol) in Solutions and Gels of Selected Hydrophilic Polymers," *Macromolecules* 32(13), 4375-4382.

We claim:

1. An allyl sulfide crosslinked hydrogel polymer network swollen in an aqueous media, wherein at least one live cell is encapsulated in the network, prepared by a process comprising the steps of:
    a) providing,
        i) a plurality of tetrafunctional poly(ethylene glycol) dibenzocyclooctyne molecules in aqueous solution,
        ii) a plurality of allyl sulfide poly(ethylene glycol) azide molecules in aqueous solution, and
        iii) at least one live cell, and
    b) mixing said tetrafunctional poly(ethylene glycol) dibenzocyclooctyne molecules in aqueous solution, said allyl sulfide poly(ethylene glycol) azide molecules in aqueous solution, and at least one live cell under conditions such that a hydrogel network is produced.

2. The hydrogel network of claim 1, wherein said network comprises an allyl sulfide crosslinked strain-promoted azide-alkyne cycloaddition hydrogel network.

3. The hydrogel network of claim 2, wherein said hydrogel network produced by a reaction between a plurality of tetrafunctional poly(ethylene glycol) dibenzocyclooctyne molecules and a plurality of allyl sulfide poly(ethylene glycol) azide molecules.

4. The hydrogel network of claim 2, wherein said allyl sulfide poly(ethylene glycol) comprises allyl sulfide bis-($PEG_3$-azide).

5. The hydrogel network of claim 2, wherein said hydrogel network comprises a wound dressing.

6. The composition of claim 1, wherein said cells are human cells.

7. An allyl sulfide crosslinked strain-promoted azide-alkyne cycloaddition hydrogel polymer network swollen in an aqueous media, wherein at least one live cell encapsulated in the network and wherein said hydrogel network is in contact with a photoinitiator, prepared by a process comprising the steps of:
    a) providing,
        i) a plurality of tetrafunctional poly(ethylene glycol) dibenzocyclooctyne molecules in aqueous solution,
        ii) a plurality of allyl sulfide poly(ethylene glycol) azide molecules in aqueous solution,
        iii) at least one live cell, and
        iv) a photoinitiator,
    b) mixing said tetrafunctional poly(ethylene glycol) dibenzocyclooctyne molecules in aqueous solution, said allyl sulfide poly(ethylene glycol) azide molecules in aqueous solution, photoinitiator, and at least one live cell under conditions such that a hydrogel network is produced.

8. The hydrogel network of claim 7, wherein said photoinitiator is in solution and at least part of said network is submerged in said solution.

9. The hydrogel network of claim 7, wherein said photoinitiator further comprises a free monothiol.

10. The hydrogel network of claim 9, wherein said free monothiol comprises mPEG-SH.

11. The hydrogel network of claim 7, wherein said hydrogel network comprises a network reaction between a plurality of tetrafunctional poly(ethylene glycol) dibenzocyclooctyne molecules and a plurality of allyl sulfide poly(ethylene glycol) azide molecules.

12. The hydrogel network of claim 7, wherein said allyl sulfide poly(ethylene glycol) comprises allyl sulfide bis-($PEG_3$-azide).

13. The hydrogel network of claim 7, wherein said photoinitiator comprises lithium phenyl-2,4,6-tri-methylbenzoylphosphinate.

14. A method of producing an allyl sulfide crosslinked strain-promoted azide-alkyne cycloaddition (SPAAC) hydrogel network, comprising:
    a) providing,
        i) a plurality of tetrafunctional poly(ethylene glycol) dibenzocyclooctyne molecules,
        ii) a plurality of allyl sulfide poly(ethylene glycol) ($PEG-N_3$) molecules, and
    b) mixing said tetrafunctional poly(ethylene glycol) dibenzocyclooctyne molecules and said allyl sulfide poly(ethylene glycol) molecules under conditions such that a hydrogel network is produced.

15. The method of claim 14, wherein said allyl sulfide poly(ethylene glycol) comprises allyl sulfide bis-($PEG_3$-azide).

16. A method comprising the steps of:
    a) providing,
        i) a plurality of tetrafunctional poly(ethylene glycol) dibenzocyclooctyne molecules in aqueous solution,
        ii) a plurality of allyl sulfide poly(ethylene glycol) azide molecules in aqueous solution,
        iii) at least one live cell, and
        iv) a photoinitiator,
    b) mixing said tetrafunctional poly(ethylene glycol) dibenzocyclooctyne molecules in aqueous solution, said allyl sulfide poly(ethylene glycol) azide molecules in aqueous solution, at least one live cell, and photoinitiator under conditions such that a hydrogel network is produced.

17. The method of claim 16, wherein mixing said photoinitiator comprises immersing said hydrogel network in an aqueous solution of photoinitiator.

* * * * *